US008759610B2

(12) United States Patent
Taylor et al.

(10) Patent No.: US 8,759,610 B2
(45) Date of Patent: Jun. 24, 2014

(54) *LYSO*-PHOSPHATIDIC ACID ACYLTRANSFERASE FROM *TROPAEOLUM MAJUS*

(75) Inventors: David C. Taylor, Saskatoon (CA); Tammy Francis, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 286 days.

(21) Appl. No.: 13/254,474

(22) PCT Filed: Feb. 3, 2010

(86) PCT No.: PCT/CA2010/000146
§ 371 (c)(1),
(2), (4) Date: Sep. 2, 2011

(87) PCT Pub. No.: WO2010/099594
PCT Pub. Date: Sep. 10, 2010

(65) Prior Publication Data
US 2011/0321195 A1 Dec. 29, 2011

Related U.S. Application Data

(60) Provisional application No. 61/202,507, filed on Mar. 5, 2009, provisional application No. 61/213,032, filed on Apr. 30, 2009.

(51) Int. Cl.
*C12N 15/82* (2006.01)
*C12N 15/87* (2006.01)
*C12N 9/10* (2006.01)
*C12N 15/00* (2006.01)
*C07H 21/04* (2006.01)
*A01H 5/10* (2006.01)

(52) U.S. Cl.
USPC ........ 800/281; 800/306; 435/193; 435/320.1; 435/468; 536/23.2; 536/23.6

(58) Field of Classification Search
None
See application file for complete search history.

(56) References Cited

U.S. PATENT DOCUMENTS

| | | | |
|---|---|---|---|
| 5,824,858 A | 10/1998 | Davies et al. | |
| 5,910,630 A | 6/1999 | Davies et al. | |
| 6,184,355 B1 * | 2/2001 | James et al. | 530/370 |
| 2007/0204370 A1 | 8/2007 | Mietkiewska et al. | |

FOREIGN PATENT DOCUMENTS

| | | |
|---|---|---|
| WO | 95/27791 | 10/1995 |
| WO | 00/29585 | 5/2000 |
| WO | 20061052807 | 5/2006 |
| WO | 2007/141257 | 12/2007 |
| WO | 2008/006207 | 1/2008 |

OTHER PUBLICATIONS

Dubois et al 2007 European Journal of Lipid Science Technology 109: p. 710-732.*

International Preliminary Report on Patentability dated Sep. 6, 2011 on on PCT-CA2010-000146.
Written Opinion and International Search Report dated May 18, 2010 on PCT-CA2010-000146.
Altschul SF, Gish W, Miller W, Myers EW, Lipman DJ. (1990) Basic local alignment search tool. J Mol Biol. 215: 403-410.
Bernerth R, Frentzen M. (1990) Utilization of erucoyl-COA by acyltransferases from developing seeds of *Brassica napus* (L.) involved in triacylglycerol biosynthesis. Plant Sci. 67: 21-28.
Bonaldo MF, Lennon G, Soares MB. (1996) Normalization and Subtraction: Two Approaches to Facilitate Gene Discovery. Genome Research. 6: 791-806.
Brough CL, Coventry JM, Christie WW, Kroon JTM, Brown AP:, Barsby TL, Slabas AR. (1996). Towards genetic engineering of triacylglycerols of defined fatty acid composition: Major changes in erucic acid content at the sn-2 position affected by the introduction of a 1-acyl-sn-glycerol-3-phosphate acyltransferase from Limnanthes douglasii into oil seed rape. Mol. Breeding. 2:133-142.
Cao Y-Z, Oo K-C, Huang AHC. (1990) Lysophosphatidate acyltransferase in the microsomes from maturing seeds of meadowfoam. (*Limnanthes alba*). Plant Physiol. 94: 1199-1206.
Coleman J. (1990) Characterization of *Escherichia coli* cells deficient in 1-acyl-sn-glycerol-3-phosphate acyltransferase activity. J Biol Chem. 265: 17215-17221.
Coleman J. (1992) Characterization of the *Escherichia coli* gene for 1-acyl-sn-glycerol-3-phosphate acyltransferase (plsc). Mol Gen Genet. 232: 295-303.
Cooper JA, Esch FS, Taylor SS, Hunter T. (1984). Phosphorylation sites in enolase and lactate dehydrogenase utilized by tyrosine protein kinases in vivo and in vitro. J. Biol. Chem. 259: 7835-7841.
Deleage G, Roux B. (1987) an algorithm for protein secondary structure prediction based on class prediction. Protein Engineering. 1: 289-294.
Derksen JTP, Cuperus FP, Kolster P. (1995) Paints and coatings from renewable resources. Industrial Crops and Products. 3: 225-236.
Han J, Lühs W, Sonntag K, Zähringer U, Borchardt DS, Wolter FP, Heinz E, Frentzen M. (2001) Functional characterization of β-ketoacyl-CoA synthase genes from *Brassica napus* L. Plant Mol. Biol. 46: 229-239.
Hanke C, Wolter FP, Coleman J, Peterek G, and Frentzen M (1995) A plant acyltransferase involved in triacylglycerol biosynthesis complements an *Escherichia coli* sn-1-acylglycerol-3-phosphate acyltransferase mutant. Eur J Biochem. 232: 806-810.
Hofman K. (2000) A superfamily of membrane-bound O-acyltransferases with implications for Wnt signaling. Trends Bioch. Sci. 25: 11-112.
Kim Hu, Li Y, Huang AHC. (2005) Ubiquitous and Endoplasmic Reticulum—Located Lysophosphatidyl Acyltransferase, LPAT2, Is Essential for Female but Not Male Gametophyte Development in *Arabidopsis*. Plant Cell. 17: 1073-1089.

(Continued)

*Primary Examiner* — David T Fox
*Assistant Examiner* — Matthew Keogh
(74) *Attorney, Agent, or Firm* — Laura Catherine Eckenswiller

(57) ABSTRACT

The cloning and broad characterization of a lyso-phosphatidic acid acyltransferase (LPAT2) from *Tropaeolum majus* is described. The TmLPAT2 enables the production of plants, seeds and cells with enhanced oil and/or fatty acid content. In particular, recombinant TMLPAT2 increases levels of very long chain fatty acids (VLCFA), especially erucic acid, in plants, seeds and cells.

10 Claims, 10 Drawing Sheets

(56) References Cited

OTHER PUBLICATIONS

Lassner MW, Levering CK, Davies HM, Knutzon DS. (1995) Lysophosphatidic Acid Acyltransferase from Meadowfoam Mediates Insertion of Erucic Acid at the sn-2 Position of Triacylglycerol in Transgenic Rapeseed Oil. Plant Physiol. 109: 1389-1394.

Leonard EC. (1993) High-erucic vegetable oils. Industrial Crops and Products. 1: 119-123.

Lohden I, Bernerth R, Frentzen M. (1990) Acyl-CoA:l-acylglycerol-3-phosphate acyltransferase from developing seeds of *Limnanthes douglasii* (R.Br.) and *Brassica napus* (L.). In PJ Quinn, JL Harwood, eds, Plant Lipid Biochemistry, Structure and Utilization. Portland Press, London, pp. 175-177.

Lohden I, Frentzen M. (1992) Triacylglycerol biosynthesis in developing seeds of *Tropaeolum majus* L. and *Limnanthes douglasii* R. Br. Planta. 188: 215-224.

Mcvetty PBE, Scarth S. (2002) Breeding for improved oil quality in *Brassica* oilseed species. J. Crop. Prod. 5: 345-369.

Mietkiewska E, Giblin EM, Wang S, Barton DL, Dirpaul J, Brost JM, Katavic V, Taylor DC. (2004) Seed-specific heterologous expression of a *T. majus* FAE gene in *Arabidopsis* results in a dramatic increase in the proportion of erucic acid. Plant Physiol. 136: 2665-2675.

Mietkiewska E, Hoffman TL, Brost JM, Giblin EM, Barton DL, Francis T, Zhang Y, Taylor DC. (2008) Hairpin-RNA mediated silencing of endogenous FAD2 gene combined with heterologous expression of *Crambe abyssinica* FAE gene causes an increase in the level of erucic acid in transgenic *Brassica carinata* seeds. Mol Breeding. 22: 619-627.

Murphy DJ, Mukherjee KD. (1988) Biosynthesis of very long chain monounsaturated fatty acids by subcellular fractions of developing seeds. FEBS Lett. 230: 101-104.

Murphy DJ, Richards D, Taylor R, Capdevielle J, Guillmont J-C, Grison R, Fairbairn D, Bowra S. (1994) Manipulation of seed oil content to produce industrial crops. Ind Crops Products. 3: 17-27.

Nagiec MM, Wells GB, Lester RL, Dickson, RC. (1993) A suppressor gene that enables *Saccharomyces cerevisiae* to grow without making sphingolipids encodes a protein that resembles an *Escherichia coli* fatty acyltransferase. J Biol Chem. 268: 22156-22163.

Nakai K, Kanehisa M. (1992) A knowledge base for predicting protein localization sites in eukaryotic cells. Genomics. 14: 897-911.

Nakashima H, Nishikawa K, Ooi T. (1986) The folding type of a protein is relevant to the amino acid composition. Journal of Biochemistry (Tokyo). 99: 153-162.

OO K-C, Huang AHC. (1989) *Lysophosphatidate acyltransferase* activities in the microsomes from palm endosperm, maize scutellum, and rapeseed cotyledons of maturing seeds. Plant Physiol. 91: 1288-1295.

Page RDM. (1996) Treeview: An application to display phylogenetic trees on personal computers. Computer Applications in the Biosciences. 12: 357-358.

Peterek G, Schmidt V, Wolter FP, Frentzen M. (1992) Approaches for cloning 1-acylglycerol acyltransferase from oilseeds. In A Cherif, ed, Metabolism, Structure and Utilization of Plant Lipids. CNP Press, Tunis, Tunisia, pp. 401-404.

Pollard MR, Stumpf PK. (1980) Long chain (C20 and C22) fatty acid biosynthesis in developing seeds of *Tropaeolum majus*, an in vivo study. Plant Physiol. 66: 641-648.

Puyaubert J, Garcia C, Chevalier S, Lessire R. (2005) Acyl-CoA elongase, a key enzyme in the development of high-erucic acid rapeseed? Eur. J. Lipid Sci. Technol. 107: 263-267.

Scarth R, Tang J. (2006) Modification of *Brassica* oil using conventional and transgenic approaches. Crop Sci. 46: 1225-1236.

Stahl U, Stalberga K, Stymne,S, Ronne H. (2008) A family of eukaryotic lysophospholipid acyltransferases with broad specificity. FEBS Letters. 582: 305-309.

Taylor DC, Thomson LW, MacKenzie SL, Pomeroy MK and Weselake RJ. (1990) Target Enzymes for Modification of Seed Storage Lipids. In: Sixth Crucifer Genetics Workshop Proceedings, (J.R. McFerson, S. Kresovich and S.G. Dwyer, eds), USDA-ARS Plant Genetic Resources Unit, Cornell University, Geneva, NY, pp. 38-39.

Taylor DC, Barton DL, Rioux KP, Reed DW, Underhill EW, MacKenzie SL, Pomeroy MK, Weber N. (1992) Biosynthesis of acyl lipids containg very-long chain fatty acids in microspore derived and zygotic embryos of *Brassica napus* L. cv. Reston. Plant Physiol. 99: 1609-1618.

Taylor DC, MacKenzie SL, McCurdy AR, McVetty PBE, Giblin EM, Pass EW, Stone SJ, Scarth R, Rimmer SR, Pickard MD. (1994) Stereospecific Analyses of Triacylglycerols from High Erucic *Brassicaceae*: Detection of Erucic Acid at the sn-2 Position in *B. oleracea* L. Genotypes. J. Am. Oil Chem. Soc. 71: 163-167.

Taylor DC, Barton DL, Giblin EM, MacKenzie SL, van den Berg K, McVetty PBE. (1995a) Microsomal Lyso-Phosphatidic Acid Acyltransferase from a *Brassica oleracea* Cultivar Incorporates Erucic Acid into the sn-2 Position of Seed Triacylglycerols. Plant Physiology. 109: 409-420.

Taylor DC, Giblin EM, Reed DW, Olson DJ, Hogge LR, MacKenzie SL. (1995b) Stereospecific Analysis and Mass Spectrometry of Triacylglycerols from *Arabidopsis thaliana* (L.) Heynh. Columbia Seed. J. Am. Oil Chem. Soc. 72: 305-308.

Taylor DC, Guo Y, Katavic V, Mietkiewska E, Francis T, Bettger W. (2008) New Seed Oils for Improved Human and Animal Health and as Industrial Feedstocks: Genetic Manipulation of the *Brassicaceae* to Produce Oils Enriched in Nervonic Acid. For H. Krishnan (ed) "Modification of Seed Composition to Promote Health and Nutrition". In Press.

Vereshchagin, The Sixteenth International Symposium on Plant Lipids (Budapest, Hungary, Jun. 1-4, 2004), Russian Journal of Plant Physiology, vol. 52, No. 3,2005, pp. 414-420. Translated from Fiziologiya Rastenii, vol. 52, No. 3, 2005, pp. 467-474.

Weier D, Hanke C, Eickelkamp A, Lühs W, Dettendorfer J, Schaffert E, Möllers C, Friedt W, Wolter FP, Frentzen M. (1997) Trierucoylglycerol biosynthesis in transgenic plants of rapeseed (*Brassica napus* L.). Fett/Lipid. 99: 160-165.

Xu J, Francis T, Mietkiewska E, Giblin EM, Barton DL, Zhang Y, Zhang M, Taylor DC. (2008). Cloning and characterization of an acyl-CoA-dependent diacylglycerol acyltransferase 1 (DGAT1) gene from *Tropaeolum majus*, and a study of the functional motifs of the DGAT protein using site-directed mutagenesis to modify enzyme activity and oil content. Plant Biotechnology J. 6: 799-818.

GenBank Accession No. FJ984563, Sep. 19, 2009.

Sonntag Nov. (1995) Industrial utilization of long-chain fatty acids and their derivatives. In *Brassica* Oilseeds (Kimber, D.S. and McGregor, D.I., eds), CAB International, Oxon, UK, pp. 339-352.

\* cited by examiner

DT | TMAEM0GH
CL885Contig1 (2 members)
    LPAT2 Contig containing 2 members:
    TMAEM2GH plate 49, well B1 & TMAEM2GH plate 40, well D2

```
ttccaccaatcctaaactatttctcgtataatcttcagttttctgaaactataagatttattgaactca
ttactctttctactaatcatcagatcgttttttttttaatctcataaatcaatctcttttgtacatcta
ttaatttctcgcttttttataaactcaaatcttcagtgtttgtccattgcaagcttcgacctatcctcg
cgagtactatgtcagttgcagcggcagctatcgtcttgccttgggcttctcttttcttctccggcc
ttgttgtcaatcttattcaggcaatattttatgttctcgtccgaccgctctctaagagtacatacagaa
ggatcaatcgggtagtggcagaattgttatggctggaacttgtatggctcattgattggtgggcaggag
ttaagatcaaattattcacagatcgtgagacctacatcagatgggtaaagagcacgcacttgtcatat
gcaatcacagaagtgacattgactgctcgtaggctgggttttggctcagcggtcaggctgccttggca
gttcattagctgttatgaagaagtcatccaaattcctaccggttataggatggtcaatgtggttttctg
agtatcttttctggaaagaagctgggcaaaggatgaaagcacattaaagtcaggtcttcagcgtctga
acgactatcctcaaccctttggttggccctctctgtggaaggaactcgcttcacacaggcaaagcttt
tagccgcgcaggagtatgcaacctcaacgggactacctgtgcctagaaatgttttgatccctcgaacta
agggttttgtatcagctgcaagtaatatgcgctcgtttgtgccagccatttatgatgtcacactggcta
ttcctaaaacctcacctccacctactatgctcagactcttcaagggcaatcatctgtggtgcatgtgc
acctcaagagacacttgatgaaggaattgccagaaacagataatgatgtggcacaatggtgcaaagaca
tatttgtggcgaaggataatttattggacaaacataaaaccgaatctacattcggtgaccaagatttgc
aggacattggtcgaccctgaagtctcttttggttgttatttcttgggcttgcttgcttatatctgggg
ctttgaagtttctcattgggtcagcactattatcctcatggaagggcattgtcatatcagcatctggtt
tgggtcttgttactgttcttatgcagacattgattcttttctcacagtcggagcgttcaacttcagcaa
agattgggtcagcaaatggagaggaaagacgaaccaaacatcagtaa
```

Fig. 3 – SEQ ID NO: 1

```
MSVAAAAIVLPLGLLFFFSGLVVNLIQAIFYVLVRPLSKSTYRRINRVVAELLWLELVWLIDWWAGVKI
KLFTDRETLHQMGKEHALVICNHRSDIDWLVGWVLAQRSGCLGSSLAVMKKSSKFLPVIGWSMWFSEYL
FLERSWAKDESTLKSGLQRLNDYPQPFWLALFVEGTRFTQAKLLAAQEYATSTGLPVPRNVLIPRTKGF
VSAASNMRSFVPAIYDVTLAIPKTSPPPTMLRLFKGQSSVVHVHLKRHLMKELPETDNDVAQWCKDIFV
AKDNLLDKHKTESTFGDQDLQDIGRPLKSLLVVISWACLLISGALKFLIGSALLSSWKGIVISASGLGL
VTVLMQTLILFSQSERSTSAKIGSANGEERRTKHQ
```

Fig. 4A – SEQ ID NO: 2

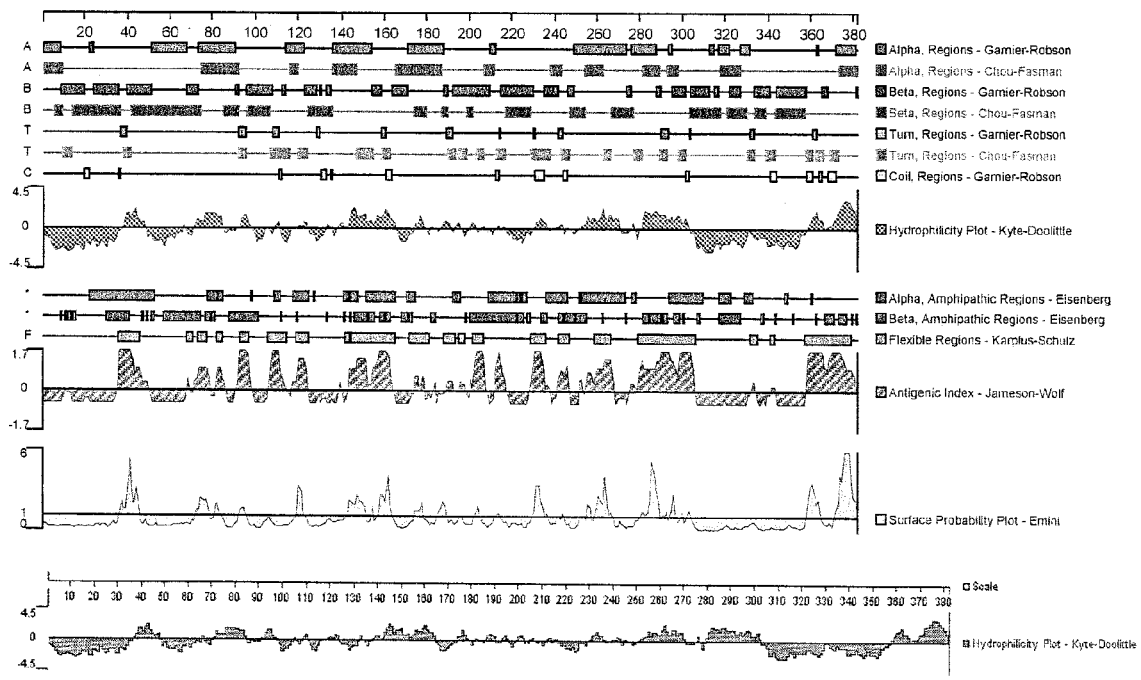

Fig. 4B

```
Predicted Structural Class of the Whole Protein: Alpha
Deléage & Roux Modification of Nishikawa & Ooi 1987

Analysis Whole Protein
Molecular Weight              42.585 kD
Length                        380 aa
1 microgram =                 23.482 pMoles
Molar Extinction coefficient  82130±5%
1 A(280) =                    0.52 mg/ml
Isoelectric Point             9.60
Charge at pH 7                14.14

Whole Protein

Amino Acid(s)           Number count    % by weight    % by frequency

Charged (RKHYCDE)       91              28.64          23.95
Acidic (DE)             30              8.60           7.89
Basic (KR)              43              14.19          11.32
Polar (NCQSTY)          88              21.76          23.16
Hydrophobic (AILFWV)    166             43.99          43.68
A Ala                   28              4.67           7.37
C Cys                   4               0.97           1.05
D Asp                   15              4.05           3.95
E Glu                   15              4.55           3.95
F Phe                   18              6.22           4.74
G Gly                   22              2.95           5.79
H His                   8               2.58           2.11
I Ile                   21              5.58           5.53
K Lys                   24              7.22           6.32
L Leu                   55              14.62          14.47
M Met                   8               2.46           2.11
N Asn                   9               2.41           2.37
P Pro                   15              3.42           3.95
Q Gln                   14              4.21           3.68
R Arg                   19              6.97           5.00
S Ser                   36              7.36           9.47
T Thr                   19              4.51           5.00
V Val                   31              7.22           8.16
W Trp                   13              5.68           3.42
Y Tyr                   6               2.30           1.58
B Asx                   0               0.00           0.00
Z Glx                   0               0.00           0.00
X Xxx                   0               0.00           0.00
. Ter                   1               0.00           0.26
```

Fig. 4B - continued

MSVAAAAIVLPLGLLFFFSGLVVNLIQAIFYVLVRPLSKSTYRRINRVVAELLWLELVWLID

I

WWAGVKIKLFTDRETLHQMGKEHALVIQ|NHRSDID|WLVGWVLAQRSGCLGSSLAVMKKSSKF

II　　　　　　　　　　　　　　　　　　　　　　　　　　III

|LPVIGW|SMWFSEYLFLERSWAKDESTLKSGLQRLNDYPQPF|WLALFVEGTRF|TQAKLLAAQE

IV　　　　　　　　　*

YATSTGLPVPR|NVLIPRTKGFF|YSAASNM|RSFVPAIYDVTLA|IPKTSPPPTMLRLFKGQSSV

VHVHLKRHLMKELPETDNDVAQWCKDIFVAKDNLLDKHKTESTFGDQDLQDIGRPLKSL

LVVISWACLLISGALKFLIGSALLSSWKGIVISASGLGLVTVLMQTLILFSQSERSTSAKIG

SANGEERRTKHQ

**Key motifs of *T majus* LPAT2 Primary Sequence**

Box I-IV motifs are conserved among related LPATs in various plant species (Kim, Li & Huang, 2005):

- Box I Conserved MBOAT motif (NHXXXXD): NHRSDID in position 91 – 97 (Hofmann, 2000)

- Box II LPVIGW

- Box III ("EGT" box)

- Box IV (NVLIPRTKGF)

- \* *Putative tyrosine phosphorylation site* $R^{215}$-$(X)_6$-$Y^{222}$-$(X)_4$-$A^{227}$ (a characteristic motif consisting of an arginine at position -7, tyrosine at position 0, and glycine/alanine at position +5 (Cooper et al., 1984)

- The sequence FVEGTR(F/S) is conserved among these plant LPATs as well as the *E. coli* LPAT (*plsC;* Coleman, 1990; 1992) and the *Saccharomyces cerevisiae* LPAT (*SLC1-1;* Nagiec et al., 1993)

Fig. 5

| Database | Description | Hit ID | Evalue |
|---|---|---|---|
| nr | 1-acyl-sn-glycerol-3-phosphate acyltransferase [Prunus mume] | gi|82568693| | 1e-134 |
| nr | 1-acyl-sn-glycerol-3-phosphate acyltransferase (putative) [Limnanthes douglasii] | gi|1067138| | 1e-133 |
| nr | 1-acyl-sn-glycerol-3-phosphate acyltransferase 2 (Lysophosphatidyl acyltransferase 2) gb|AAT36638.1| acyl-CoA:1-acylglycerol-3-phosphate acyltransferase [Brassica oleracea] | gi|73620927| | 1e-132 |
| nr | Phospholipid/glycerol acyltransferase [Medicago truncatula] | gi|92897607| | 1e-132 |
| nr | 1-acyl-sn-glycerol-3-phosphate acyltransferase 2 (Lysophosphatidyl acyltransferase 2) emb|CAB09138.1| acyl-CoA:1-acylglycerol-3-phosphate acyltransferase [Brassica napus] | gi|83287830| | 1e-131 |

Fig. 6A

LYSO-PHOSPHATIDIC ACID ACYLTRANSFERASE FROM *TROPAEOLUM MAJUS*

CROSS-REFERENCE TO RELATED APPLICATIONS

This application is a national entry of International Patent Application PCT/CA2001/000146 filed Feb. 3, 2010 and claims the benefit of U.S. Provisional application Ser. No. 61/202,507 filed Mar. 5, 2009, and U.S. Provisional application Ser. No. 61/213,032 field Apr. 30, 2009, the contents of all of which are herein incorporated by reference.

FIELD OF THE INVENTION

The present invention relates to lyso-phosphatidic acid acyltransferase (LPAT2) from *Tropaeolum majus*, a nucleic acid molecule encoding LPAT2 enzyme and uses of the nucleic acid molecule and/or enzyme for altering oil and/or triacylglycerol (TAG) production in organisms.

BACKGROUND OF THE INVENTION

Many groups worldwide have a vested interest in inserting genes into *Brassica napus* in an effort to produce the industrial feedstock trierucin. Erucic acid (cis-13 docosenoic acid, 22:1) is the major very long chain fatty acid (VLCFA) in the seed oil from HEAR (high erucic acid rapeseed) *Brassica napus* cultivars, accounting for 45-55% of the total fatty acids (Han 2001). HEAR cultivars are of high interest for industrial purposes because 22:1 is a valuable feedstock with more than 1000 potential or patented industrial applications (Sontaag 1995; Scarth 2006). Currently the major derivative of erucic acid is erucamide, which is used as a surface-active additive in coatings and in the production of plastic films as an anti-block or slip agent. Many other applications are foreseen for erucic acid and its hydrogenated derivative behenic acid, e.g. in lubricants, detergents, film processing agents and coatings, as well as in cosmetics and pharamceuticals (Leonard 1993; Derksen 1995; McVetty 2002; Puyaubert 2005). For many of these industrial uses, the economics are limited by the proportion of 22:1 in the seed oil. To compete with petroleum-based products, it is desirable to increase the 22:1 proportion as high as possible in order to reduce the cost of purification (Scarth 2006). In addition, the engineering of HEAR Brassicaceae to produce seed oils containing substantial trierucin would lend the intact oil to a wide range of new applications (Sonntag 1995). In general, stereospecific analyses have shown that among most members of the Brassicaceae, 22:1 is virtually excluded from the sn-2 position of TAGs (Taylor 1994); thus erucic acid is essentially found only in the sn-3 and the sn-1 positions, limiting the potential overall proportions of 22:1 to a maximum of about 66 mol %. The best genetically-unmodified HEAR *B. napus* cultivars have only about 50% erucic acid in the seed oil.

In the traditional Kennedy pathway for seed oil (triacylglycerol, TAG) biosynthesis, lyso-phosphatidic acid acyltransferase (LPAT; EC 2.3.1.51) is the major enzyme responsible for acylating the sn-2 position of the glycerol backbone and therefore largely determines the sn-2 acyl composition of TAGs. This presumably ER-based LPAT is typically referred to as an LPAT2 in most oilseed species, distinguishing it from the plastidial LPAT1 which has enzyme characteristics more like the prokaryotic LPAT found in *E. coli*.

Several studies have suggested that in *B. napus* this is at least partially due to the inability of the lyso-phosphatidic acid acyltransferase (LPAT; EC 2.3.1.51) to utilize erucoyl-CoA (Oo 1989; Bernerth 1990; Taylor 1990; Taylor 1992). Various groups worldwide have attempted or advocated the transformation of rapeseed with an LPAT gene which has the desired capacity to utilize erucoyl-CoA during TAG bioassembly (Cao 1990; Lohden 1990; Taylor 1990; Taylor 1992; Peterek 1992; Murphy 1994). LPATs from *Limnanthes* spp were originally cited as unique gene donors to accomplish this (Cao 1990; Lohden 1990; Taylor 1990; Taylor 1992; Peterek 1992; Murphy 1994). Accordingly, LPAT2s from *L. douglasii* and *L. alba* have been cloned and used to enhance sn-2 erucic proportions in *B. napus* (Brough 1996; Lassner 1995; Henke 1995) but with this single genetic modification, the enhancement of overall proportions of erucic acid and accumulation of significant trierucin have not resulted (Weier 1997). Indeed, the erucic acid was merely redistributed the sn-1 and sn-3 positions to the sn-2 position, with no significant improvement in the mol % erucic acid in seed TAGs.

There is a need to discover and characterize new higher plant LPATs which can utilize erucoyl-CoA or other VLC-CoAs and thereby be used to enhance erucic acid or other VLCFA (e.g. nervonic acid) content in organisms, especially plants, especially plants whose seed oils contain VLCFAs, more especially plants of the HEA Brassicaceae. There is a further need to discover plant LPATs which can enhance oil content of oilseeds in general.

SUMMARY OF THE INVENTION

In accordance with the present invention, there is provided an isolated, purified or recombinant nucleic acid molecule comprising the nucleotide sequence as set forth in SEQ ID NO: 1, or a complementary nucleotide sequence thereof.

There is further provided an isolated or purified polypeptide comprising the amino acid sequence as set forth SEQ ID NO: 2.

There is yet further provided a vector or construct comprising with a nucleic acid molecule of the present invention.

There is yet further provided a host cell, seed or plant transformed with a nucleic acid molecule of the present invention.

There is yet further provided a method of increasing oil and/or very long chain fatty acid (VLCFA) content in a plant, seed or cell comprising: expressing or over-expressing a nucleic acid molecule of the present invention in the plant, seed or cell to increase expression of a lyso-phosphatidic acid acyltransferase 2 in the plant, seed or cell.

Here we disclose the cloning and broad characterization of a lyso-phosphatidic acid acyltransferase (LPAT2) from *T. majus*. We show the utility of the TmLPAT2 to enable the production of plants, seeds and cells with enhanced oil and/or fatty acid content. In particular, we show the utility of recombinant TmLPAT2 to increase levels of VLCFAs, especially erucic acid. Further, these new LPATs may be used to transform oilseeds already containing VLC-enhancing genetic modifications to maximize the proportions of VLCFAs.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings:

FIG. 3. Consensus *T. majus* LPAT2 DNA sequence (SEQ ID NO: 1).

FIG. 4A. Predicted *T. majus* LPAT2 amino acid sequence (SEQ ID NO: 2).

FIG. 4B. Predicted structural class analysis of the whole *T. majus* LPAT2 protein including Kyte-Doolittle Hydrophilicity plot.

FIG. 5. Key motifs of *T. majus* LPAT2 amino acid sequence (SEQ ID NO: 2).

FIG. 6A. BLAST search of the most homologous relatives to the *T. majus* LPAT2.

DESCRIPTION OF PREFERRED EMBODIMENTS

Figure 1A:
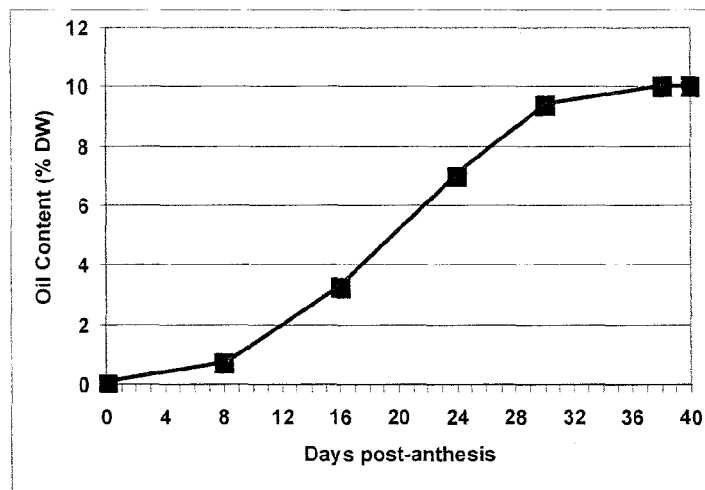
FIG. 1. (A) TAG accumulation in developing *T. majus* seed. (B) Fatty acid composition of developing *T. majus* seed. The following were the designated stages of embryo development in days post anthesis: Early: 8-15 d.p.a.; Early-mid: 16-20 d.p.a.; Mid: 22-27 d.p.a.; Mid-late: 27-30 d.p.a.; Mature: 38 d.p.a. Fatty acid composition and oil content were measured as described above.

All technical terms employed in this specification are commonly used in biochemistry, molecular biology and agriculture; hence, they are understood by those skilled in the field to which this invention belongs. Those technical terms can be found, for example in: *Molecular Cloning: A Laboratory Manual* 3rd ed., vol. 1-3, ed. Sambrook and Russel, Cold Spring Harbor Laboratory Press, Cold Spring Harbor, N.Y., 2001; *Current Protocols in Molecular Biology*, ed. Ausubel et al., Greene Publishing Associates and Wiley-Interscience, New York, 1988 (including periodic updates); *Short Protocols in Molecular Biology: A Compendium of Methods from Current Protocols in Molecular Biology* 5th ed., vol. 1-2, ed. Ausubel et al., John Wiley & Sons, Inc., 2002; *Genome Analysis: A Laboratory Manual*, vol. 1-2, ed. Green et al., Cold Spring Harbor Laboratory Press, Cold Spring Harbor, N.Y., 1997. Methodology involving plant biology techniques are described here and also are described in detail in treatises such as *Methods in Plant Molecular Biology: A Laboratory Course Manual*, ed. Maliga et al., Cold Spring Harbor Laboratory Press, Cold Spring Harbor, N.Y., 1995. These reference are herein incorporated by reference.

The term "altering" or "increasing" in respect of oil content or fatty acid content refers to changing the level of one or more of these properties relative to the level for a similar cell, tissue or whole organism that was not transformed with the nucleic acid molecule of the present invention.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein.

As used herein, "expression" denotes the production of an RNA product through transcription of a gene or the production of the protein product encoded by a nucleotide sequence.

"Over-expression" or "up-regulation" is used to indicate that expression of a particular gene sequence or variant thereof, in a cell or plant, including all progeny plants derived thereof, results in a LPAT2 enzyme whose activity has been increased by genetic engineering, relative to a control cell or plant.

Nucleic acid molecules of the present invention may be transformed into and/or expressed or over-expressed in cells, tissues and/or whole organisms. Tissues may be, for example, seed tissues of a plant. Organisms may be, for example, plants, animals (e.g. insects) or microorganisms (e.g. yeast). Plants of particular interest, and cells and tissues thereof, may include, for example, oilseed plants. Oilseed plants include, for example, Brassicaceae spp. (e.g. rapeseed and Canola), *Borago* spp. (borage), *Ricinus* spp. (e.g. *Ricinus communis* (castor)), *Theobroma* spp. (e.g. *Theobroma cacao* (cocoa bean)), *Gossypium* spp. (cotton), *Crambe* spp., *Cuphea* spp., *Linum* spp. (flax), *Lesquerella* spp., *Limnanthes* spp., Linola, *Tropaeolum* spp. (nasturtium), *Olea* spp. (olive), *Elaeis* spp. (palm), *Arachis* spp. (peanut), *Carthamus* spp. (safflower), *Glycine* spp. (soybean), *Soja* spp. (soybean), *Helianthus* spp.

(sunflower), *Vernonia* spp. Oilseed plants of particular note are from the family Brassicaceae, especially *Arabidopsis, Brassica napus, Brassica rapa, Brassica carinata, Brassica juncea,* and *Camelina sativa*. Other plant species of interest include, for example, *Zea mays* (corn), *Oenothera* spp., *Nicotiana* spp. (e.g. tobacco), *Triticum* spp. (e.g. wheat), *Hordeum* spp. (e.g. barley), *Oryza* spp. (e.g. rice), *Avena* spp. (e.g. oat), *Sorghum* spp. (e.g. sorghum), *Secale* spp. (e.g. rye) and other members of the Gramineae. Some particular plant species include Canola, HEAR *B. napus,* HEAR *B. carinata,* LEAR *B carinata, B. juncea, B. rapa, B. oleracea, Camelina, Flax, Crambe,* Soybean, Corn, *Lesquerella,* Castor, Olive, *T. majus, Lunaria, T. speciosum,* California Bay and *Cardamine greaca,* including genetically modified oilseed plants (e.g. high laurate *B. napus,* high nervonic *B. carinata*).

EXAMPLE 1

Plant Materials and Growth Conditions

*Tropaeolum majus* seeds (cultivar Dwarf Chemy Rose) were obtained from Early's Farm and Garden Centre, Saskatoon, SK, and were grown at the Kristjanson Biotechnology Complex greenhouses, Saskatoon, under natural light conditions supplemented with high-pressure sodium lamps with a 16 h photoperiod (16 h of light and 8 h of darkness) at 22° C. and a relative humidity of 25 to 30%. Flowers were hand-pollinated and seeds at various stages of development were harvested, their seed coats were removed and embryos were frozen in liquid nitrogen and stored at −80° C. The lipid composition of developing nasturtium embryos at various stages of development were conducted. The following were the designated stages of embryo development in days post anthesis: Early: 8-12 d.p.a.; Early-mid: 13-20 d.p.a.; Mid: 22-27 d.p.a.; Mid-late: 27-30d.p.a.; Mature: 35 d.p.a.

EXAMPLE 2

Analysis of Oil Accumulation in Developing *Tropaeolum majus* Embryos

Freeze-dried *T. majus* embryos of early, mid and late stages, as well as mature seeds, were weighed and transferred to a cooled mortar and ground in 2 ml IPA:$CH_2Cl_2$ (2:1), the mixture was transferred to a test tube; to this was added the above solvent (1 ml) and 0.9% NaCl (1 ml) and vortexed. 2 ml $CH_2Cl_2$ was added, the mixture re-vortexed and centrifuged at 2500 r.p.m. for 3 min. The $CH_2Cl_2$ layer was removed, the extraction repeated and the $CH_2Cl_2$ layers combined. $CH_2Cl_2$: Benzene:Methanol (1:1:1) (1 ml) was added and then the sample evaporated to dryness. The dried sample was resuspended in $CHCl_3$ (1 ml) to give the total lipid extract (TLE). The developmental acyl composition of the TLE and the total oil content at each stage were determined by transesterification followed by GC using tri-15:0 as an internal standard and tri-17:0 as an external standard (to determine completeness of transmethylation) as described previously (Mietkiewska 2004). A stereospecific analysis of a TLC-purified TAG fraction was performed as described by Taylor et al. (Taylor 1995b) (Table 1).

Referring to Table 1, stereospecific analyses were performed as described by Taylor et al. (Taylor 1995a). Total TAG reports the acyl composition of the TAG fraction isolated from a total lipid extract. In Set A, the distribution of all acyl moieties at each sn-position is reported (read left to right). In Set B, the distribution of each acyl moiety spanning all three sn-positions is reported (read top to bottom). The distribution of the VLCMFAs 20:1 and 22:1 are bolded.

TABLE 1

| | Fatty Acyl Distribution (% wt/wt)[a] | | | | | | | | | | | |
|---|---|---|---|---|---|---|---|---|---|---|---|---|
| | 16:0 | 18:0 | 18:1 | 18:2 | 18:3 | 20:0 | 20:1 | 22:0 | 22:1 | 24:0 | 24:1 | Total |
| Total TAG Set A | 0.7 | 0.1 | 2.1 | Tr[b] | 0.4 | 0 | 16.6 | 0.5 | 78.3 | 0 | 1.4 | 100 |
| sn-1 | 4.0 | 4.4 | 2.8 | 0.8 | 0 | 0 | 13.2 | 0 | 64.7 | 0 | 1.0 | 100 |
| sn-2 | 1.5 | 0.9 | 3.0 | 0 | 0.4 | 0 | 12.1 | 0.3 | 75.7 | 0 | 0.5 | 100 |
| sn-3 | 2.1 | 4.1 | 2.2 | 0 | 0 | 0 | 14.3 | 1.5 | 73.6 | 0 | 2.2 | 100 |
| Set B | | | | | | | | | | | | |
| sn-1 | 52.6 | 46.8 | 35.0 | 100.0 | 0 | 0 | 33.3 | 0 | 30.2 | 0 | 27.0 | |
| sn-2 | 19.7 | 9.6 | 37.5 | 0 | 100.0 | 0 | 30.6 | 16.7 | 35.4 | 0 | 13.5 | |
| sn-3 | 27.6 | 43.6 | 27.5 | 0 | 0 | 0 | 36.1 | 83.3 | 34.4 | 0 | 59.5 | |
| Total | 100 | 100 | 100 | 100 | 100 | 0 | 100 | 100 | 100 | 0 | 100 | |

Figure 1B:
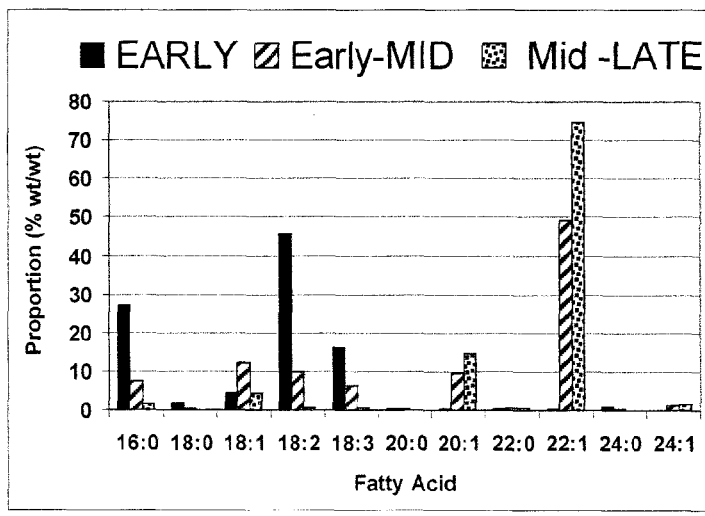

[a] >95% of total GC FAME peaks accounted for in all cases
[b] tr = <0.05% wt/wt; minor traces of other fatty acyl moieties not shown Referring to FIG. 1A and FIG. 1B, based on the peak of erucic acid accumulation and oil content profile, it was assumed that, like other Kennedy pathway enzymes (e.g. *T. majus* DGAT1 cloned and characterized previously (Xu 2008)), LPAT would also be at its peak expression and activity at the highest point of the exponential phase of embryo growth. For nasturtium, the peak of oil deposition (about 16% oil as % of DW) and the maximal erucic acid proportion therein (about 78% wt/wt), occurred in the mid-late developmental stage, typically 20-26 days post-anthesis. Thus, the mid-late developing stage (arrow in FIG. 1A) was chosen for embryo harvest and storage at −80° C.

EXAMPLE 3

*T majus* cDNA Library Construction and Normalization cDNA was synthesized from mRNA isolated from mid-developing nasturtium embryos using a cDNA synthesis kit (Stratagene). The cDNA was directionally cloned into the pBluescript SK II (+) vector (Stratagene) and transformed into DH10B electrocompetent cells. The primary library was amplified using semi-solid agar (SeaPrep agarose, Mandel).

Normalization of the library was performed at $C_0t$ 2.5 and $C_0t$ 5 following the normalization method 4 of Bonaldo et al. (Bonaldo 1997). Double stranded phagemid DNA was converted to single stranded DNA using Gene II protein and Exonuclease III (Genetrapper cDNA Positive Selection System, Gibco BRL, cat. no. 10356-020). The single stranded DNA was purified from the double stranded DNA using HAP chromatography (type II Hydroxyapatite, BioRad, cat. no. 158-4200). 20,000 ESTs from this library were sequenced as described below.

EXAMPLE 4

Sequencing and Analysis

Sequencing was performed on an ABI3730xl DNA Analyzer using a BigDye Terminator v3.1 Cycle Sequencing kit (Applied Biosystems). Sequence analyses were performed using Lasergene software (DNAStar, Madison, Wis., USA). Sequence similarity searches and other analyses were performed using BLASTN, BLASTX (Altschul 1990) and PSORT (Nakai 1992) programs. The *T. majus* LPAT2 clone was represented by a contig among 2 members of 20,000 ESTs isolated and analyzed from a normalized cDNA library prepared from mid-developing nasturtium embryos.

Figure 2:
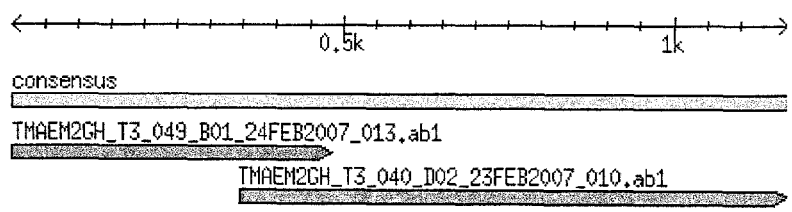
FIG. 2. Alignment of 2-member (TMAEM2 GH plate 49, well B1 and TMAEM2 GH plate 40, well D2) contig of the *T. majus* LPAT2 gene.

LPAT2-like ESTs and contigs of *T. majus* were identified and aligned. FIG. 2. shows the alignment of the 2-member (TMAEM2 GH plate 49, well B1 and TMAEM2 GH plate 40, well D2) contig of the *T. majus* LPAT2 gene.

The consensus *T. majus* LPAT2 nucleotide sequence (SEQ ID NO: 1) (1358 bp) is shown in FIG. 3 and the predicted amino acid sequence (SEQ ID NO: 2) (380 aa) of the LPAT2 enzyme is shown in FIG. 4A. FIG. 4B shows the predicted structural class Analysis of the whole TmLPAT2 protein (via program of Deléage & Roux (Deléage 1987) as modified from Nishikawa & Ooi (Nishikawa 1986)). The TmLPAT2 has a predicted molecular mass of 42.585 kD, and a PI of 9.60. Based on a Kyte-Doolittle hydrophilicity analysis, there appear to be at least 8 transmembrane regions.

Key motifs of the *T. majus* LPAT2 primary amino acid sequence are shown in FIG. 5. Box I-IV motifs are conserved among related LPATs in various plant species (Kim 2005). Referring to FIG. 5, Box I is a conserved MBOAT motif (NHXXXD): NHRSDID in position 91-97 (Hofmann 2000), Box II is a LPVIGW motif, Box III is a "EGT" box, Box IV is a NVLIPRTKGF motif, and the * Box is a putative tyrosine phosphorylation site $R^{215}$—$(X)_6$—$Y^{222}$—$(X)_4$-$A^{227}$, which is a characteristic motif consisting of an arginine at position −7, tyrosine at position 0, and glycine/alanine at position +5 (Cooper 1984). The sequence FVEGTR(F/S) is conserved among these plant LPAT2s as well as the *E. coli* LPAT (plsC; Coleman 1990; Coleman 1992) and the *Saccharomyces cerevisiae* LPAT (SLC1-1; Nagiec 1993).

Figures 6B, 6C:
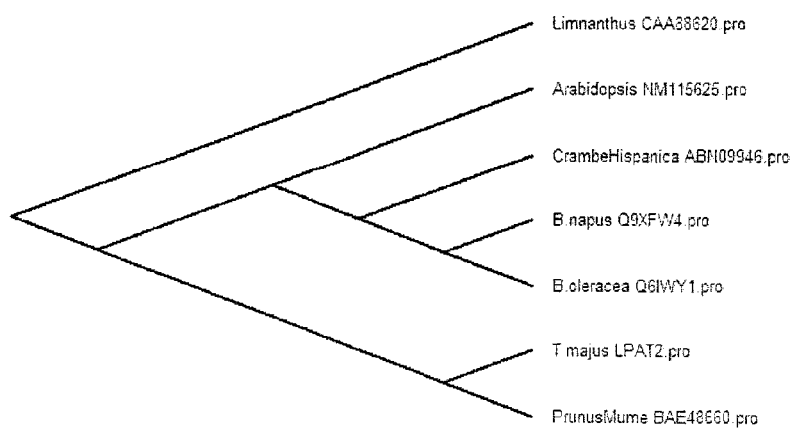
FIG. 6B. Alignment of most homologous relatives to the *T. majus* LPAT2. *T. majus* (SEQ ID NO: 2), *Arabidopsis* (SEQ ID NO: 3), *B. napus* (SEQ ID NO: 4), *B. oleracea* (SEQ ID NO: 5), *Crambe hispanica* (SEQ ID NO: 6), *Limnanthes douglasii* (SEQ ID NO: 7) and *Prunus mume* (SEQ ID NO: 8). The MBOAT Box I motif is boxed in blue which is the only box in the second row; Box II is boxed in green which is the first box in the third row; Box III motif is boxed in purple which is the second box in the third row; Box IV motif is boxed in orange which is the first box in the fourth row. Box I-IV motifs are conserved among related LPATs in various plant species (Kim 2005). The putative tyrosine phosphorylation site is boxed in red which is the second box in the fourth row, with the key Y222 Tyr$^{222}$) phosphorylation residue indicated by the arrow. Box III is also highly conserved in *E. coli*, and *Sacch. cer.*
FIG. 6C. Phylogenic tree of LPAT2s aligned via ClustalW (slow/accurate, Gonnet), constructed using TREEVIEW.

BLAST Search, alignment and phylogenetic tree assessment of *T. majus* LPAT2 and its most homologous relatives are shown in FIGS. 6A, 6B and 6C, respectively.

EXAMPLE 5

Cloning of Full Length *T. majus* (Tm) LPAT2 cDNA

Primers were designed to amplify the TmLPAT2 gene with adaptor restrictions sites (in bold italics):
GAGG*TACCGG*AAATGTCAGTTGCAGC (SEQ ID NO: 9): 26-mer 5' primer amplifying TmLPAT2 sequence with Kpn I restriction site;
CC*GCTCGAG*TTTTACTGATGTTTGGTTGC (SEQ ID NO: 10): 29-mer 3' primer amplifying TmLPAT2 sequence (+stop) with Xho I site.

Complementary DNA was synthesized from nasturtium mid-developing embryo total RNA using Superscript II (Invitrogen). The TmLPAT2 gene was amplified from the cDNA using Turbo Pfu polymerase (Stratagene) on a RoboCycler thermocycler (Stratagene) using the following program: 95° C. for 3 min, followed by 30 cycles of 95° C. for 30 sec, 55° C. for 45 sec, 72° C. for 2 min, an additional extension of 72° C. for 10 min was included, with a final holding temperature of 4° C. Amplified PCR product was digested using restriction enzymes KpnI (NEB) and XhoI (NEB). The gene was ligated into pYES/NT B (Invitrogen) using T4 ligase (Invitrogen) in a 4:1 molar ration (insert: vector) at 4° C. over two nights. Four microliters of the ligation reaction were used to transform Top10 Chemically Competent cells (Invitrogen) as per standard protocol. Putative clones were cultured in liquid medium plus selection, and grown overnight at 37° C. with shaking (250 rpm). Plasmid DNA was extracted using a QIAprep Spin miniprep kit (Qiagen). PCR screen for gene insert using GAL1N5CR primers and Taq polymerase. Program: 95° C. for 3 min; 30 cycles of 95° C. for 30 s; 52° C. for 45 s; 72° C. for 2 min; 72° C. for 10 min; 4° C. final holding temperature. Positive clones were confirmed by sequencing.

EXAMPLE 6

Cloning of Full Length *A. thaliana* (Athal) LPAT2 cDNA

Primers to amplify the Athal LPAT2 are as follows with adaptor restrictions sites (in bold italics):
CC*GGTACC*AGGATGGTGATTGCTGCAGCT (SEQ ID NO: 11): 29-mer 5' primer amplifying AtLPAT2 sequence with Kpn I restriction site;
CC*TCGAGT*GTGAGAACCAGTTTTTACTT (SEQ ID NO: 12): 29-mer 3' primer amplifying AtLPAT2 sequence (+stop) with Xho I site.

Messenger RNA was extracted from *A. thaliana* ecotype Columbia leaves using Trizol (Invitrogen). Complementary DNA was synthesized from the total RNA using Superscript II (Invitrogen). The *A. thaliana* LPAT2 was amplified from cDNA using Turbo Pfu polymerase (Stratagene) on a RoboCycler thermocycler using the following program: 95° C. for 3 min, followed by 30 cycles of 95° C. for 30 sec, 55° C. for 30 sec, 72° C. for 2 min, an additional extension of 72° C. for 10 min was included, with a final holding temperature of 4° C. Addition of 3' A-overhangs was accomplished by adding 1 µl of Taq polymerase (Invitrogen) and incubating at 72° C. for 15 minutes. The PCR product was electrophoresed on a 1% agarose gel and extracted using the QIAquick gel extraction kit (Qiagen). Four microliters of the purified fragment were ligated into pCR2.1-TOPO vector (Invitrogen). Two microliters of the ligation were used to transform Top10 Chemically Competent cells (Invitrogen) as per standard protocol. Selection was performed by Ampicillin antibiotics and blue/white screening. Putative clones were screened via colony PCR. Cells were swirled in 10 µl sterile water and lysed at 95° C. for 5 minutes. One microliter of the DNA prep was used to screen via PCR. The same primers that were used to clone the gene were used to screen for positive clones using the following program: 95° C. for 3 minutes, followed by 30 cycles of 95° C. for 30 seconds, 50° C. for 30 seconds, 72° C. for 90 seconds, an additional extension of 72° C. for 10 minutes was included, with a final holding temperature of 4° C. Positive clones were cultured and plasmid DNA extracted using the QIAprep Spin miniprep kit (Qiagen). Clones were sequenced, and gene fidelity was confirmed. TOPO-AtL-PAT2 was digested using restriction enzymes KpnI (NEB) and XhoI (NEB). The expression vector pYES NT B (Invitrogen) was also digested with KpnI and purified using the QIAquick gel extraction kit (Qiagen). The ligation was performed using T4 ligase (Invitrogen) in a 4:1 molar ration (insert: vector) at 16° C. over night. Four microliters of the ligation reaction were used to transform Top10 Chemically Competent cells (Invitrogen) as per standard protocol. Putative clones were cultured in liquid medium plus selection, and grown overnight at 37° C. with shaking (250 rpm). Plasmid DNA was extracted using a QIAprep Spin miniprep kit (Qiagen). PCR screen for gene insert using the same cloning primers and Taq polymerase. Program: 95° C. for 3 min, followed by 30 cycles of 95° C. for 30 sec, 50° C. for 30 sec, and 72° C. for 90 sec, an additional extension of 72° C. for 10 min was included, with a final holding temperature of 4° C.

EXAMPLE 7

Transformation of Y03749 Yeast LPAT (SLC1$^-$) Deletion Mutant Strain with Tm LPAT2 or Athal LPAT2

Yeast strain Y03749 (slc1Δ, MATα his3Δ1 leu2Δ0 met15Δ0 ura3Δ0 YDL052c::KanMX4) was transformed with the pYES2 NT B-AthalLPAT2 or with pYES2 NT B-TmLPAT2 or with empty pYES2 NT B vector using the small scale yeast transformation method from the pYES2 NT B manual. Clones were selected on plates containing (SC-Uracil+2% Glucose).

Confirmation of transformation: DNA from putative positive clones was extracted using a quick plasmid extraction method. A single colony was picked into 200 µl lysis buffer (100 mM NaCl, 10 mM Tris-HCl pH 8.0, 1 mM EDTA, and 0.1% SDS). An equal volume of acid washed beads (0.5 mm diameter) was added along with 200 µl phenol:choloroform (2:1). Mix (vortex) sample for 30 seconds. Further extract using a slow rotation for 5 minutes. Centrifuge for 5 minutes at 13000 rpm on a bench top microcentrifuge (Eppendorf). Recover aqueous phase, precipitate DNA using 2× volume of ethanol and 0.1× volumes of 3 M sodium acetate. Incubate sample at −80° C. for 30 minutes. Centrifuge at 13000 rpm, 15 minutes. Wash DNA pellet using 80% ethanol. Centrifuge for 5 minutes at 13000 rpm. Air dry pellet and re-suspend DNA in 50 µl TE buffer. DNA concentration was measured using a NanoDrop ND-1000 spectrophotometer. Top10 Chemically Competent cells (Invitrogen) were transformed with the purified DNA as per standard protocol. Colonies were screened via PCR and restriction digests by methods previously mentioned.

EXAMPLE 8

T. majus LPAT2 and Athal LPAT2 Expression in Y03749 Yeast LPAT (SLC1$^-$) Deletion Mutant and Assays of LPAT Activity Starter cultures of the Y03749 ™ LPAT2, Y03749 Athal LPAT2 or Y03749 plasmid only (control) transformants were grown in minimal medium (SC-Uracil+2% Glucose) at 30° C. with shaking at 250 rpm. Culture density was measured using $OD_{595}$, and sufficient culture to produce an $OD_{595}$=0.4 in 50 ml of Induction Medium (SC-Uracil+2% Galactose+1% Raffinose) was centrifuged, washed and re-suspended in Induction Medium. Culture was induced at 30° C. with shaking (250 rpm) for 8 hour, 16 hour, 24 hour, or 48 hour. The maximum expression of the Tm LPAT2 recombinant protein was found after a 24 hour induction; the Athal LPAT2 expression was maximal at 48 hr of induction. Induced cells were harvested by centrifugation and protein was extracted using the glass bead/bead beater method. Protein concentration was measured using Bradford reagent (in triplicate), and the protein was used immediately for the LPAT assay.

LPAT assays of the recombinant protein fraction from each transformant were conducted as described by Taylor et al. (Taylor 1995a) using either $^{14}$C 18:1-CoA or $^{14}$C 22:1-CoA as the acyl donor and 18:1-LPA or 22:1-LPA as the acyl acceptor. The resolution of the $^{14}$C-labeled phosphatidic acid (PA) product by TLC run in ethyl acetate/iso-octane/acetic acid (45/15/10) was as described by Taylor et al. (Taylor 1995a).

Figure 7:
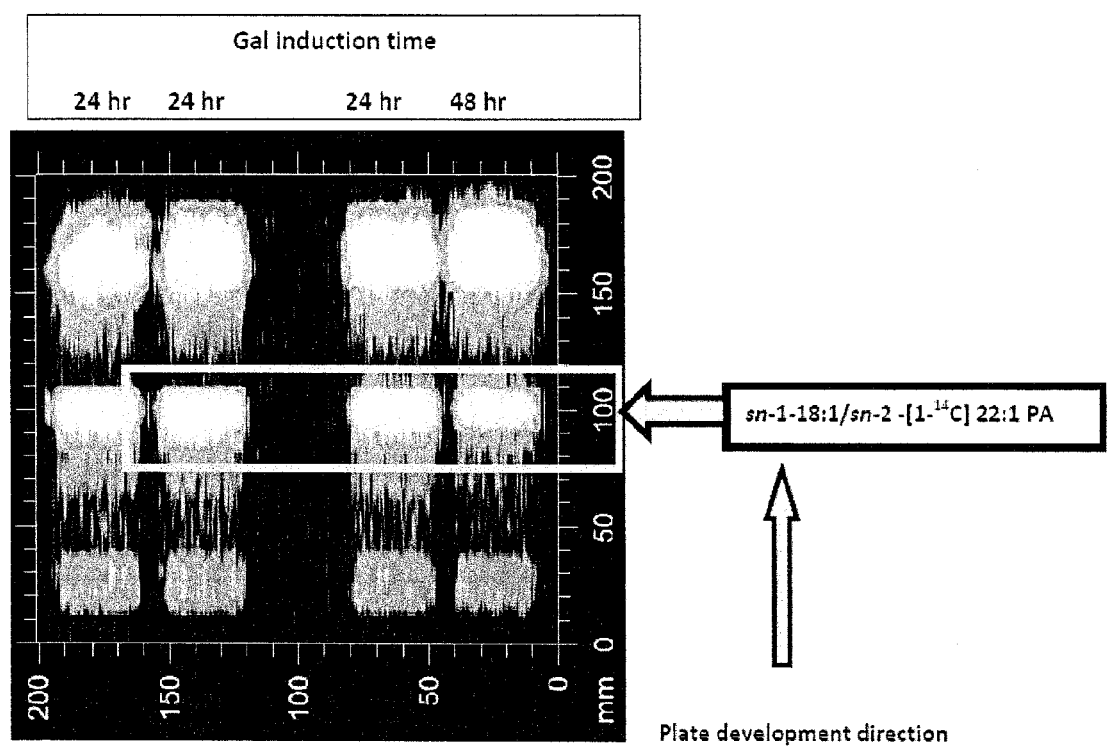
FIG. 7. TLC plate of radiolabeled TLE from LPAT assay of protein fraction from 24 or 48 hour-induced cultures of yeast LPAT$^-$ (SLC$^-$) mutant Y03749 expressing recombinant *T. majus* LPAT2. Assays were conducted in the presence of 18:1-LPA+1-$^{14}$C 22:1-CoA. The arrow shows the radiolabeled sn-1 18:1/sn-2 [1-$^{14}$C] 22:1 PA product. The expression of the recombinant TmLPAT2 enzyme reached a maximum at 24 hr of Gal induction. Plate development direction is from bottom to top.
Figure 8:
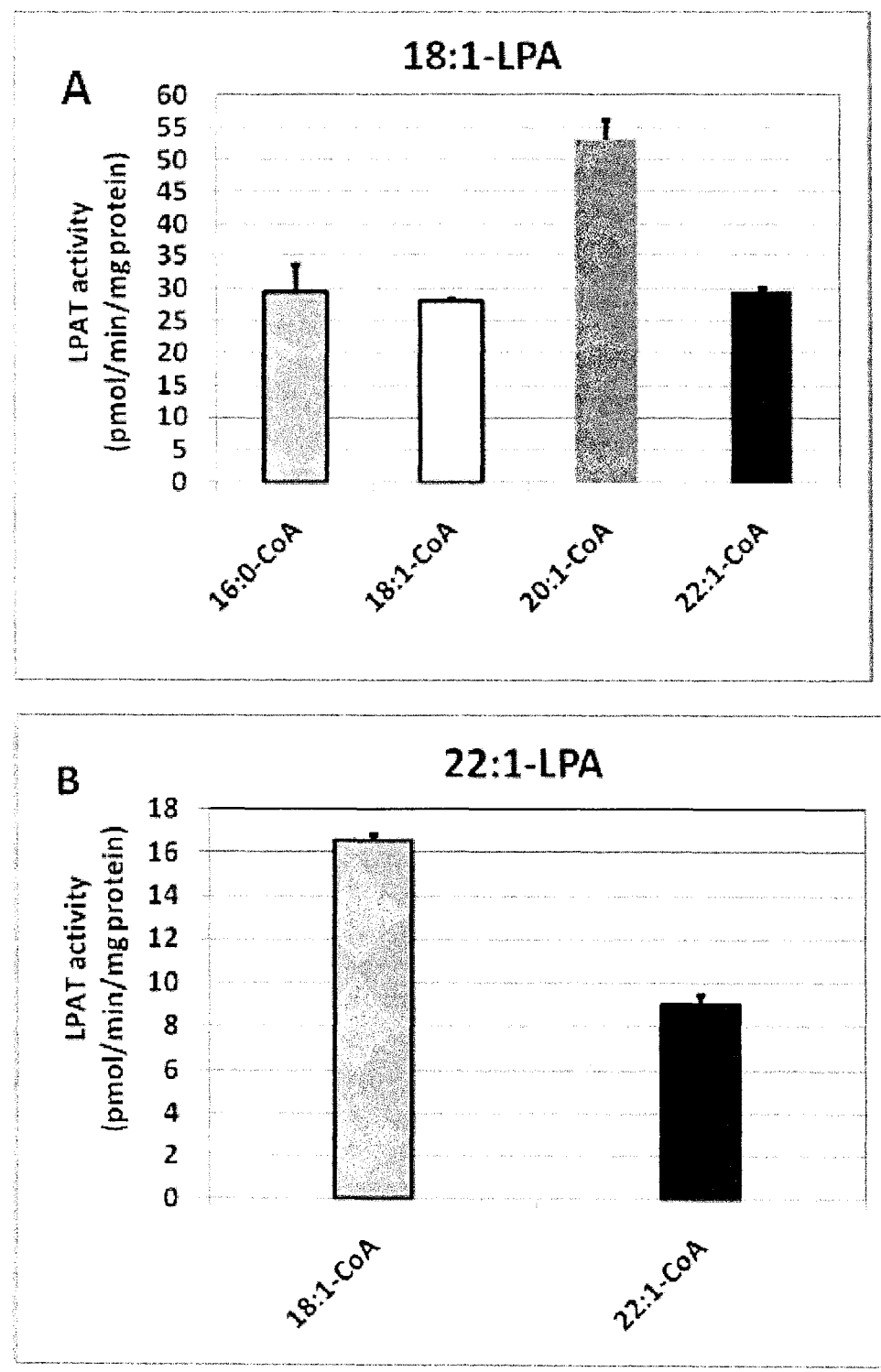
FIG. 8. LPAT assay of protein fraction from 24 hour-induced cultures of yeast LPAT$^-$ (SLC$^-$) mutant Y03749 expressing the recombinant *T. majus* LPAT2. Assays were conducted in the presence of (A): 18:1-LPA+ either 1-$^{14}$C 16:0-CoA, 1-$^{14}$C 18:1-CoA, 1-$^{14}$C 20:1-CoA or 1-$^{14}$C 22:1-CoA; (B): 22:1-LPA+ either 1-$^{14}$C 18:1-CoA or 1-$^{14}$C 22:1-CoA. LPAT specific activity is expressed as pmol sn-2-labeled phosphatidic acid (PA) formed/min/mg protein.

The heterologously-expressed TmLPAT2 was able to incorporate 22:1-CoA into the sn-2 position of 18:1-LPA (FIG. 7). Maximum expression was observed after 24 hours of induction. In the presence of 18:1-LPA as acceptor, the heterologously-expressed TmLPAT was able to utilize a range of acyl-CoA substrates (FIG. 8A) with its highest activity observed with 20:1-CoA; the activity with 16:0-CoA, 18:1-CoA and 22:1-CoA were all about the same. The very strong ability of the Tm LPAT2 to utilize 20:1-CoA, incorporating 20:1 into the sn-2 position of LPA (even stronger than the ability to use 18:1-CoA or 22:1-CoA), is a distinct relative specificity of the Tm LPAT2 not observed with the *Limnanthes* LPAT2. The Tm LPAT2 erucoyl-CoA activity was up to 90% of that observed with oleoyl-CoA, showing that the Tm LPAT2 is indeed capable of utilizing 22:1-CoA effectively, almost as effectively as 18:1-CoA. This relative acyl preference profile for the recombinant Tm LPAT2 is unique compared to that reported by Brown et al. (Brown 1995) using recombinant *L. douglasii* LPAT2 expressed in an *E. coli* LPAT$^-$ (SLC$^-$) mutant strain JC201. *L. douglasii* LPAT2 22:1-CoA activity was only approx 30% of that observed with oleoyl-CoA. The TmLPAT2 was also able to use 22:1-LPA as an acceptor in the presence of either 18:1-CoA or 22:1-CoA as the acyl donor. The 22:1-CoA LPAT2 activity with 22:1-LPA was about 50% of that observed with the 18:1-CoA donor (FIG. 8B).

Figure 9:
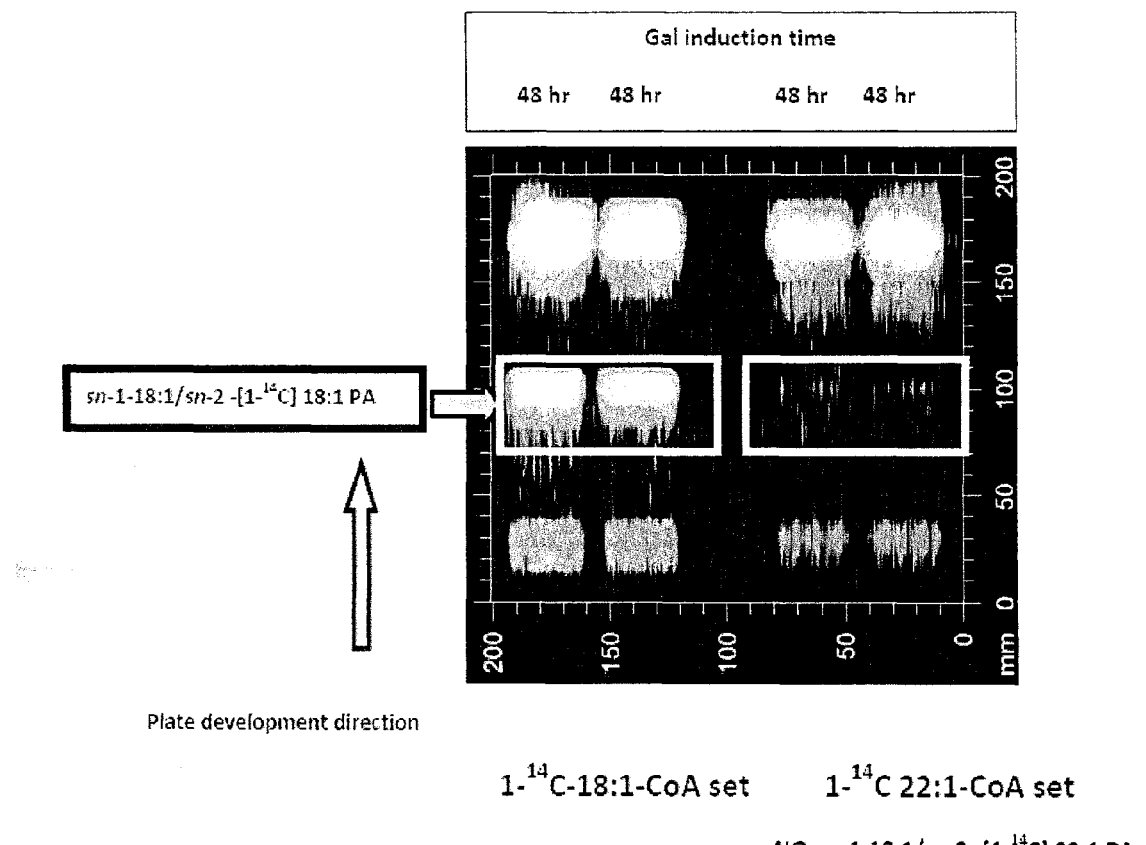
FIG. 9. TLC plate of radiolabeled TLE from LPAT assay of protein fraction from 48-hour-induced cultures of yeast mutant Y03749 expressing recombinant Athal LPAT2 protein. Assays were conducted in the presence of either 18:1-LPA+1-$^{14}$C 18:1-CoA, or in the presence of 18:1-LPA+1-$^{14}$C-22-CoA. The arrow shows the radiolabeled sn-1 18:1/sn-2 [1-$^{14}$C] 18:1 PA product. Note that in the 1-$^{14}$C-22:1-CoA reactions, there is no significant production of labeled PA. The expression of the recombinant Athal LPAT2 enzyme reached a maximum at 48 hr of Gal induction. Plate development direction is from bottom to top.

The heterologously-expressed AtLPAT2 was able to incorporate 18:1-CoA into the sn-2 position of 18:1-LPA (FIG. 9). Maximum expression was observed after 48 hours of induction. However, the AtLPAT2 was unable to incorporate 22:1 into the sn-2 position of 18:1-LPA.

EXAMPLE 9

Figure 10:
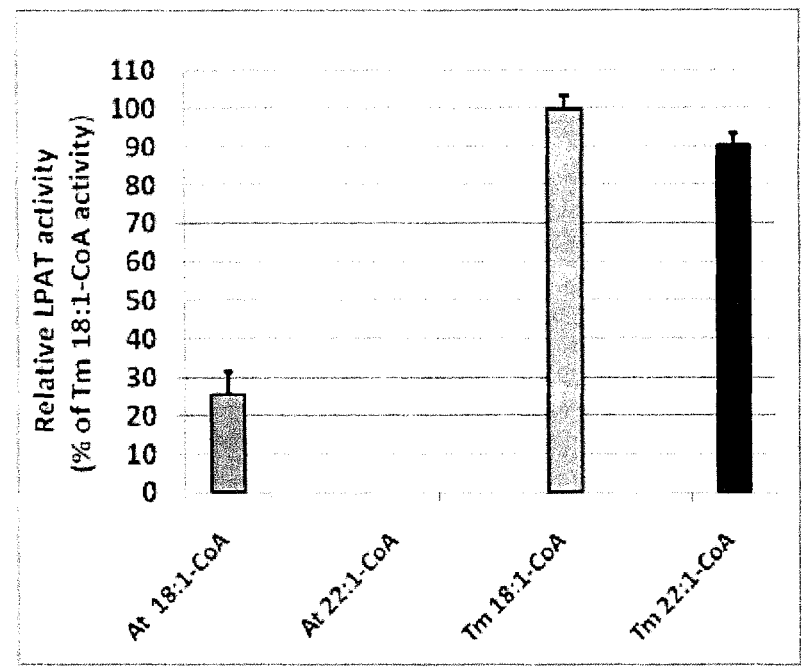
FIG. 10. Comparison of recombinant *T. majus* LPAT2 (Tm) and Athal LPAT2 (At) activities in yeast transformant microsomal fractions. *Arabidopsis thaliana* (Athal) and *Tropaeolum majus* (Tmaj) LPAT2 activities were measured in microsomal fractions prepared from 48 hour induction, and 24 hr induction cultures, respectively, assayed in the presence of 18:1-LPA and either $^{14}$C 18:1-CoA or $^{14}$C 22:1-CoA.

Comparison of Recombinant Tm LPAT2 and Athal LPAT2 Activities Expressed in Microsomal Fractions from Yeast Y03749 Transformants In comparing the TmLPAT2 and AthalLPAT2 activities at maximal expression, the specific activity of the expressed Tm LPAT2 with oleoyl-CoA as substrate was approx 4-fold higher than the corresponding activity with AtLPAT2 (FIG. 10). The *Arabidopsis* LPAT2 was able to use oleoyl-CoA, but unable to use erucoyl-CoA, a trend identical to that observed with a *B. napus* Topas LPAT2 positive control system.

Figure 11:
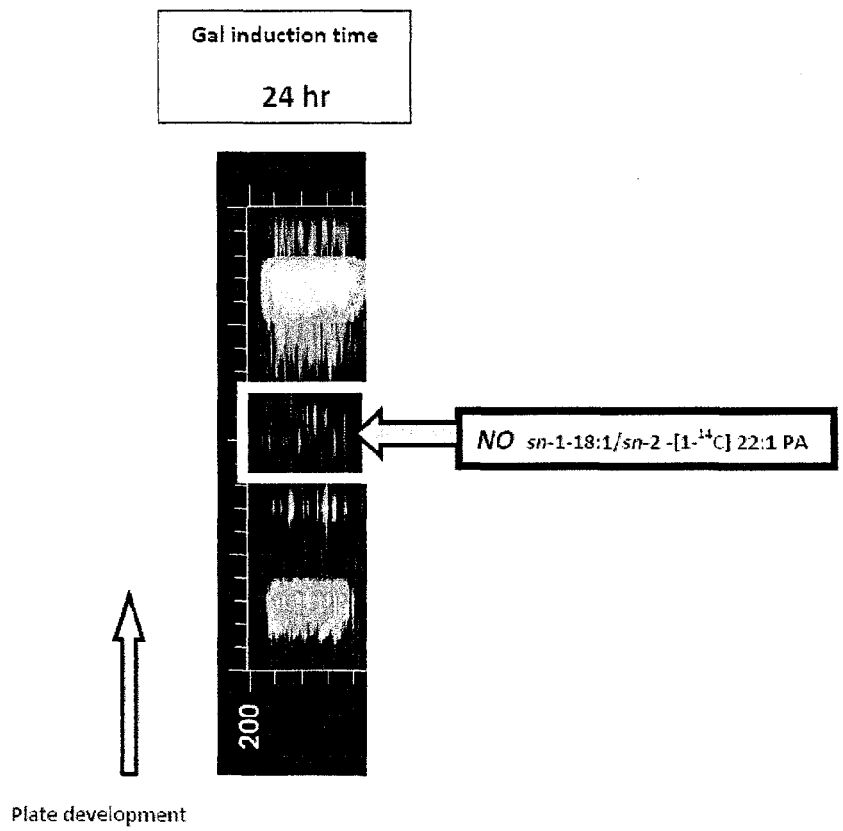
FIG. 11. TLC plate of radiolabeled TLE from LPAT assay of protein fraction from 24 hr induced culture of yeast LPAT$^-$ (SLC$^-$) mutant Y03749 transformed with empty plasmid only. The LPAT assay was conducted in the presence of 18:1-LPA+1-$^{14}$C 22:1-CoA. The arrow shows the absence of radiolabeled sn-1 18:1/sn-2 [1-$^{14}$C] 22:1 PA product. Plate development direction is from bottom to top.

While there has recently been another lyso-phospholipid acyltransferase discovered in yeast (ScLPLAT), it differs from the specific lysophosphatidic acid acyltransferase that is encoded by SLC1 in that it cannot efficiently use lysophosphatidic acid produced by acylation of glycerol-3-phosphate in vitro; rather, it prefers LPC or LPE (Stahl 2008). In the control Y03749 LPAT⁻ (SLC⁻) mutant transformed with empty plasmid, wherein the ScLPLAT activity is still present, there is no significant acylation of LPA with $^{14}$C 22:1-CoA in our assay (FIG. 11). This indicates that the contribution of ScLPLAT to the erucoyl PA product produced in the TmLPAT2 Y03479 transformants, is negligible and clearly confirms that the Tm erucoyl-CoA:LPAT2 activity expressed in the Y03749 mutant background is not due to the ScLPLAT. Thus, the ScLPLAT is not a significant contributing factor to any LPA acylating activity expressed in the LPAT⁻ (SLC⁻) deletion mutant Y03749. However, in the Y03749 strain, in agreement with Stahl et al (Stahl 2008), there was significant LPCAT activity (LPLAT activity) observed with 18:1-CoA+ 18:1-LPC (but not with 22:1-CoA+18:1-LPC).

The present findings with the cloned and ectopically-expressed *T. majus* LPAT2 gene show that the encoded product can utilize erucoyl-CoA to acylate the sn-2 position of LPA, and at a rate almost identical to that observed with oleoyl-CoA. This is in contrast to the in vitro data reported by Lohden and Frentzen (Lohden 1992) which showed the complete inability of the *T. majus* LPAT2 to use erucoyl-CoA in the presence of 18:1 LPA in vitro. Thus, despite there being about a dozen plant LPAT2s that have been cloned to date, the cloning and strong erucoyl-CoA utilizing properties of the present *T. majus* LPAT2 is unexpected. It is known that highly homologous predicted protein sequences can encode members of the same family of enzymes which nonetheless may have widely varying catalytic substrate specificities not apparent from their primary sequences. For example, of the five putative LPATs listed in FIG. 6A using an homology (BLAST) algorithm, only those from *Limnanthes* spp have been shown to possesses erucoyl-CoA LPAT2 activity (Lassner 1995). For example, the *Limnanthes douglasii* sequence gi I1067138 I with an homology score of 1e-133 is known to be an erucoyl-utilizing LPAT2 while the albeit homologous *B. napus* sequence gi I 83287830 I with score of 1e-131, and the *Prunus mume* gi I 82568693 I, do not exhibit any capacity to utilize erucoyl moieties. The selective characteristics of the protein sequences that encode these enzymes and which lead to erucoyl specificity vs. non specificity are not currently understood by those skilled in the art.

Predictions of acyl specificity of LPAT2s has arisen primarily from biochemical studies involving LPAT enzyme assays of microsomal fractions from developing seeds. Previous studies of the LPAT2s from a number of oilseeds had suggested that the *T. majus* LPAT was not involved in synthesis of trierucin because microsomal preparations from developing *T. majus* embryos exhibited little or no LPAT activity with erucoyl-CoA (Cao 1990; Lohden 1992). Furthermore, biochemical evidence reported based on microsomal LPAT enzyme assays of a high erucic *B. oleracea* landrace indicated that the LPAT could utilize erucoyl-CoA in vitro (Taylor 1995a). However, its capacity to do so proved to be untrue once the gene was cloned in 2004; upon ectopic expression the actual capacity of the gene product to use erucoyl-CoA was not observed. Thus, the current demonstration of the capability of the cloned TmLPAT2 to utilize erucoyl-CoA was not expected.

Accordingly, the expression of the *T. majus* LPAT2 clone in high erucic Brassicaceae (e.g. the high erucic *B. carinata* lines co-expressing the *Crambe* KCS and an RNAi-silenced FAD 2 (Mietkiewska 2008) or in high nervonic *B. carinata* lines (expressing a *Lunaria* KCS or *Cardamine* KCS (Taylor 2008) may be utilized to enhance the overall proportions of VLCFAs in the sn-2 position of TAGs and increase the probability of producing, for example, trierucin or trinervonin. High VLCFA hosts may include HEAR *B. napus, B. carinata, Crambe, T. majus* or genetically modified lines of these plant hosts.

It is also significant that the specific activity of the expressed TmLPAT2 with oleoyl-CoA as substrate was approx 4-fold higher than the corresponding activity with AthalLPAT2. Thus, it is expected that expression of the *T. majus* LPAT2 clone in any or all oilseeds can be used to enhance oil content and seed weight. Specific applications for enhancing oil content and seed weight may be used in the following hosts: Canola, HEAR *B. napus*, HEAR *B. carinata*, LEAR *B carinata, B. juncea, B. rapa, B. oleracea, Camelina*, Flax, *Crambe*, Soybean, Corn, *Lesquerella*, Castor, Olive, *T. majus, Lunaria, T. speciosum*, California Bay, *Cardamine greaca* and all other genetically modified oilseeds (e.g. high laurate *B. napus*, high nervonic *B. carinata*).

REFERENCES

The contents of the entirety of each of which are incorporated by this reference.

Altschul S F, Gish W, Miller W, Myers E W, Lipman D J. (1990) Basic local alignment search tool. *J Mol Biol*. 215: 403-410.

Bernerth R, Frentzen M. (1990) Utilization of erucoyl-COA by acyltransferases from developing seeds of *Brassica napus* (L.) involved in triacylglycerol biosynthesis. *Plant Sci*. 67: 21-28.

Bonaldo M F, Lennon G, Soares M B. (1996) Normalization and Subtraction: Two Approaches to Facilitate Gene Discovery. *Genome Research*. 6: 791-806.

Brough C L, Coventry J M, Christie W W, Kroon J T M, Brown A P, Barsby T L, Slabas A R. (1996). Towards genetic engineering of triacylglycerols of defined fatty acid composition: Major changes in erucic acid content at the sn-2 position affected by the introduction of a 1-acyl-sn-glycerol-3-phosphate acyltransferase from *Limnanthes douglasii* into oil seed rape. *Mol. Breeding*. 2:133-142.

Cao Y-Z, Oo K-C, Huang A H C. (1990) Lysophosphatidate acyltransferase in the microsomes from maturing seeds of meadowfoam. (*Limnanthes alba*). *Plant Physiol*. 94: 1199-1206.

Coleman J. (1990) Characterization of *Escherichia coli* cells deficient in 1-acyl-sn-glycerol-3-phosphate acyltransferase activity. *J Biol Chem*. 265: 17215-17221.

Coleman J. (1992) Characterization of the *Escherichia coli* gene for 1-acyl-sn-glycerol-3-phosphate acyltransferase (plsc). *Mol Gen Genet*. 232: 295-303.

Cooper J A, Esch F S, Taylor S S, Hunter T. (1984). Phosphorylation sites in enolase and lactate dehydrogenase utilized by tyrosine protein kinases in vivo and in vitro. *J. Biol. Chem*. 259: 7835-7841.

Deléage G, Roux B. (1987) An algorithm for protein secondary structure prediction based on class prediction. *Protein Engineering*. 1: 289-294.

Derksen J T P, Cuperus F P, Kolster P. (1995) Paints and coatings from renewable resources. *Industrial Crops and Products*. 3: 225-236.

Han J, Lühs W, Sonntag K, Zähringer U, Borchardt D S, Wolter F P, Heinz E, Frentzen M. (2001) Functional characterization of β-ketoacyl-CoA synthase genes from *Brassica napus* L. *Plant Mol. Biol*. 46: 229-239.

Hanke C, Wolter F P, Coleman J, Peterek G, and Frentzen M (1995) A plant acyltransferase involved in triacylglycerol biosynthesis complements an *Escherichia coli* sn-1-acylglycerol-3-phosphate acyltransferase mutant. *Eur J Biochem*. 232: 806-810.

Hofman K. (2000) A superfamily of membrane-bound O-acyltransferases with implications for Wnt signaling. *Trends Bioch. Sci.* 25: 11-112.

Kim H U, Li Y, Huang A H C. (2005) Ubiquitous and Endoplasmic Reticulum-Located Lysophosphatidyl Acyltransferase, LPAT2, Is Essential for Female but Not Male Gametophyte Development in *Arabidopsis*. *Plant Cell.* 17: 1073-1089.

Lassner M W, Levering C K, Davies H M, Knutzon D S. (1995) Lysophosphatidic Acid Acyltransferase from Meadowfoam Mediates Insertion of Erucic Acid at the sn-2 Position of Triacylglycerol in Transgenic Rapeseed Oil. *Plant Physiol.* 109: 1389-1394.

Leonard E C. (1993) High-erucic vegetable oils. *Industrial Crops and Products.* 1: 119-123.

Lohden I, Bernerth R, Frentzen M. (1990) Acyl-CoA:1-acylglycerol-3-phosphate acyltransferase from developing seeds of *Limnanthes douglasii* (R. Br.) and *Brassica napus* (L). In P J Quinn, J L Harwood, eds, *Plant Lipid Biochemistry, Structure and Utilization*. Portland Press, London, pp 175-177.

Lohden I, Frentzen M. (1992) Triacylglycerol biosynthesis in developing seeds of *Tropaeolum majus* L. and *Limnanthes douglasii* R. Br. *Planta.* 188: 215-224.

McVetty P B E, Scarth S. (2002) Breeding for improved oil quality in *Brassica* oilseed species. *J. Crop. Prod.* 5: 345-369.

Mietkiewska E, Giblin E M, Wang S, Barton D L, Dirpaul J, Brost J M, Katavic V, Taylor D C. (2004) Seed-specific heterologous expression of a *T. majus* FAE gene in *Arabidopsis* results in a dramatic increase in the proportion of erucic acid. *Plant Physiol.* 136: 2665-2675.

Mietkiewska E, Hoffman T L, Brost J M, Giblin E M, Barton D L, Francis T, Zhang Y, Taylor D C. (2008) Hairpin-RNA mediated silencing of endogenous FAD2 gene combined with heterologous expression of *Crambe abyssinica* FAE gene causes an increase in the level of erucic acid in transgenic *Brassica carinata* seeds. *Mol Breeding.* 22: 619-627.

Murphy D J, Mukherjee K D. (1988) Biosynthesis of very long chain monounsaturated fatty acids by subcellular fractions of developing seeds. *FEBS Lett.* 230: 101-104.

Murphy D J, Richards D, Taylor R, Capdevielle J, Guillmont J-C, Grison R, Fairbairn D, Bowra S. (1994) Manipulation of seed oil content to produce industrial crops. *Ind Crops Products.* 3: 17-27.

Nagiec M M, Wells G B, Lester R L, Dickson, R C. (1993) A suppressor gene that enables *Saccharomyces cerevisiae* to grow without making sphingolipids encodes a protein that resembles an *Escherichia coli* fatty acyltransferase. *J Biol Chem.* 268: 22156-22163.

Nakai K, Kanehisa M. (1992) A knowledge base for predicting protein localization sites in eukaryotic cells. *Genomics.* 14: 897-911.

Nakashima H, Nishikawa K, Ooi T. (1986) The folding type of a protein is relevant to the amino acid composition. *Journal of Biochemistry* (Tokyo). 99: 153-162.

Oo K-C, Huang A H C. (1989) Lysophosphatidate acyltransferase activities in the microsomes from palm endosperm, maize scutellum, and rapeseed cotyledons of maturing seeds. *Plant Physiol.* 91: 1288-1295.

Page R D M. (1996) TREEVIEW: An application to display phylogenetic trees on personal computers. *Computer Applications in the Biosciences.* 12: 357-358.

Peterek G, Schmidt V, Wolter F P, Frentzen M. (1992) Approaches for cloning 1-acylglycerol acyltransferase from oilseeds. In A Chemf, ed, *Metabolism, Structure and Utilization of Plant Lipids*. CNP Press, Tunis, Tunisia, pp 401-404.

Pollard M R, Stumpf P K. (1980) Long chain (C20 and C22) fatty acid biosynthesis in developing seeds of *Tropaeolum majus*, an in vivo study. *Plant Physiol.* 66: 641-648.

Puyaubert J, Garcia C, Chevalier S, Lessire R. (2005) Acyl-CoA elongase, a key enzyme in the development of high-erucic acid rapeseed? *Eur. J. Lipid Sci. Technol.* 107: 263-267.

Scarth R, Tang J. (2006) Modification of *Brassica* oil using conventional and transgenic approaches. *Crop Sci.* 46: 1225-1236.

Sonntag N O V. (1995) Industrial utilization of long-chain fatty acids and their derivatives. In *Brassica Oilseeds* (Kimber, D. S. and McGregor, D. I., eds), CAB International, Oxon, UK, pp. 339-352.

Stahl U, Stalberga K, Stymne, S, Ronne H. (2008) A family of eukaryotic lysophospholipid acyltransferases with broad specificity. *FEBS Letters.* 582: 305-309.

Taylor D C, Thomson L W, MacKenzie S L, Pomeroy M K and Weselake R J. (1990) Target Enzymes for Modification of Seed Storage Lipids. In: *Sixth Crucifer Genetics Workshop Proceedings*, (J. R. McFerson, S. Kresovich and S. G. Dwyer, eds), USDA-ARS Plant Genetic Resources Unit, Cornell University, Geneva, N.Y., pp 38-39.

Taylor D C, Barton D L, Rioux K P, Reed D W, Underhill E W, MacKenzie S L, Pomeroy M K, Weber N. (1992) Biosynthesis of acyl lipids containg very-long chain fatty acids in microspore derived and zygotic embryos of *Brassica napus* L. cv. Reston. *Plant Physiol.* 99: 1609-1618.

Taylor D C, MacKenzie S L, McCurdy A R, McVetty P B E, Giblin E M, Pass E W, Stone S J, Scarth R, Rimmer S R, Pickard M D. (1994) Stereospecific Analyses of Triacylglycerols from High Erucic Brassicaceae: Detection of Erucic Acid at the sn-2 Position in *B. oleracea* L. Genotypes. *J. Am. Oil Chem. Soc.* 71: 163-167.

Taylor D C, Barton D L, Giblin E M, MacKenzie S L, van den Berg K, McVetty P B E. (1995a) Microsomal Lyso-Phosphatidic Acid Acyltransferase from a *Brassica oleracea* Cultivar Incorporates Erucic Acid into the sn-2 Position of Seed Triacylglycerols. *Plant Physiology.* 109: 409-420.

Taylor D C, Giblin E M, Reed D W, Olson D J, Hogge L R, MacKenzie S L. (1995b) Stereospecific Analysis and Mass Spectrometry of Triacylglycerols from *Arabidopsis thaliana* (L.) Heynh. Columbia Seed. *J. Am. Oil Chem. Soc.* 72: 305-308.

Taylor D C, Guo Y, Katavic V, Mietkiewska E, Francis T, Bettger W. (2008) New Seed Oils for Improved Human and Animal Health and as Industrial Feedstocks: Genetic Manipulation of the Brassicaceae to Produce Oils Enriched in Nervonic Acid. For H. Krishnan (ed) "Modification of Seed Composition to Promote Health and Nutrition". In Press.

Weier D, Hanke C, Eickelkamp A, LUhs W, Dettendorfer J, Schaffert E, Milers C, Friedt W, Wolter F P, Frentzen M. (1997) Trierucoylglycerol biosynthesis in transgenic plants of rapeseed (*Brassica napus* L.). *Fett/Lipid.* 99: 160-165.

Xu J, Francis T, Mietkiewska E, Giblin E M, Barton D L, Zhang Y, Zhang M, Taylor D C. (2008). Cloning and characterization of an acyl-CoA-dependent diacylglycerol acyltransferase 1 (DGAT1) gene from *Tropaeolum majus*, and a study of the functional motifs of the DGAT protein using site-directed mutagenesis to modify enzyme activity and oil content. *Plant Biotechnology J.* 6: 799-818.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An isolated, purified or recombinant nucleic acid molecule comprising the nucleotide sequence as set forth in SEQ ID NO: 1, or a full-length complementary nucleotide sequence thereof.

2. An isolated or purified polypeptide comprising the amino acid sequence as set forth SEQ ID NO: 2.

3. A vector or construct comprising the nucleic acid molecule of claim 1.

4. A cell, seed or plant transformed with a nucleic acid of claim 1 or a vector or construct of claim 3.

5. The cell, seed or plant according to claim 4, which is of family Brassicaceae.

6. The cell, seed or plant according to claim 4, which is of *Arabidopsis, Brassica napus, Brassica rapa, Brassica carinata, Brassica juncea* or *Camelina sativa*.

7. A method of increasing oil and/or very long chain fatty acid (VLCFA) content in a plant, seed or cell of family Brassicaceae comprising: transforming a plant, seed or cell of family Brassicaceae with the nucleic acid of claim 1, expressing or over-expressing the nucleic acid molecule of claim 1 in the transformed plant, seed or cell to increase expression of a lyso-phosphatidic acid acyltransferase 2 in the plant, seed or cell, the oil and/or VLCFA content increased in comparison to a similar plant, seed or cell not transformed with the nucleic acid molecule of claim 1.

8. The method according to claim 7, wherein erucic acid 22:1 content is increased.

9. The method according to claim 7, wherein the plant, seed or cell is of *Arabidopsis, Brassica napus, Brassica rapa, Brassica carinata, Brassica juncea* or *Camelina sativa*.

10. The method according to claim 8, wherein the plant, seed or cell is of *Arabidopsis, Brassica napus, Brassica rapa, Brassica carinata, Brassica juncea* or *Camelina sativa*.

* * * * *

SEQUENCE LISTING

<160> NUMBER OF SEQ ID NOS: 12

<210> SEQ ID NO 1
<211> LENGTH: 1358
<212> TYPE: DNA
<213> ORGANISM: Tropaeolum majus

<400> SEQUENCE: 1

```
ttccaccaat cctaaactat ttctcgtata atcttcagtt ttctgaaact ataagattta      60
ttgaactcat tactctttct actaatcatc agatcgtttt ttttttaatc tcataaatca     120
atctcttttg tacatctatt aatttctcgc tttttttataa actcaaatct tcagtgtttg    180
tccattgcaa gcttcgacct atcctcgcga gtactatgtc agttgcagcg gcagctatcg    240
tcttgccctt ggggcttctc ttttcttct ccggccttgt tgtcaatctt attcaggcaa     300
tattttatgt tctcgtccga ccgctctcta agagtacata cagaaggatc aatcgggtag    360
tggcagaatt gttatggctg gaacttgtat ggctcattga ttggtgggca ggagttaaga    420
tcaaattatt cacagatcgt gagaccttac atcagatggg taaagagcac gcacttgtca    480
tatgcaatca cagaagtgac attgactggc tcgtaggctg ggttttggct cagcggtcag    540
gctgccttgg cagttcatta gctgttatga agaagtcatc caaattccta ccggttatag    600
gatggtcaat gtggttttct gagtatcttt ttctggaaag aagctgggca aaggatgaaa    660
gcacattaaa gtcaggtctt cagcgtctga acgactatcc tcaacccttt tggttggccc    720
tctttgtgga aggaactcgc ttcacacagg caaagctttt agccgcgcag gagtatgcaa    780
cctcaacggg actacctgtg cctagaaatg ttttgatccc tcgaactaag ggttttgtat    840
cagctgcaag taatatgcgc tcgtttgtgc cagccattta tgatgtcaca ctggctattc    900
ctaaaacctc acctccacct actatgctca gactcttcaa ggggcaatca tctgtggtgc    960
atgtgcacct caagagacac ttgatgaagg aattgccaga acagataat gatgtggcac     1020
aatggtgcaa agacatattt gtggcgaagg ataatttatt ggacaaacat aaaaccgaat    1080
ctacattcgg tgaccaagat ttgcaggaca ttggtcgacc cctgaagtct cttttggttg    1140
ttatttcttg ggcttgcttg cttatatctg ggctttgaa gtttctcatt gggtcagcac     1200
tattatcctc atggaagggc attgtcatat cagcatctgg tttgggtctt gttactgttc    1260
ttatgcagac attgattctt ttctcacagt cggagcgttc aacttcagca aagattgggt    1320
cagcaaatgg agaggaaaga cgaaccaaac atcagtaa                            1358
```

<210> SEQ ID NO 2
<211> LENGTH: 380
<212> TYPE: PRT
<213> ORGANISM: Tropaeolum majus

<400> SEQUENCE: 2

```
Met Ser Val Ala Ala Ala Ile Val Leu Pro Leu Gly Leu Leu Phe
 1               5                  10                  15

Phe Phe Ser Gly Leu Val Val Asn Leu Ile Gln Ala Ile Phe Tyr Val
                20                  25                  30

Leu Val Arg Pro Leu Ser Lys Ser Thr Tyr Arg Arg Ile Asn Arg Val
            35                  40                  45

Val Ala Glu Leu Leu Trp Leu Glu Leu Val Trp Leu Ile Asp Trp Trp
        50                  55                  60

Ala Gly Val Lys Ile Lys Leu Phe Thr Asp Arg Glu Thr Leu His Gln
65                  70                  75                  80
```

Met Gly Lys Glu His Ala Leu Val Ile Cys Asn His Arg Ser Asp Ile
                85                  90                  95

Asp Trp Leu Val Gly Trp Val Leu Ala Gln Arg Ser Gly Cys Leu Gly
            100                 105                 110

Ser Ser Leu Ala Val Met Lys Lys Ser Ser Lys Phe Leu Pro Val Ile
        115                 120                 125

Gly Trp Ser Met Trp Phe Ser Glu Tyr Leu Phe Leu Glu Arg Ser Trp
    130                 135                 140

Ala Lys Asp Glu Ser Thr Leu Lys Ser Gly Leu Gln Arg Leu Asn Asp
145                 150                 155                 160

Tyr Pro Gln Pro Phe Trp Leu Ala Leu Phe Val Glu Gly Thr Arg Phe
                165                 170                 175

Thr Gln Ala Lys Leu Leu Ala Ala Gln Glu Tyr Ala Thr Ser Thr Gly
            180                 185                 190

Leu Pro Val Pro Arg Asn Val Leu Ile Pro Arg Thr Lys Gly Phe Val
        195                 200                 205

Ser Ala Ala Ser Asn Met Arg Ser Phe Val Pro Ala Ile Tyr Asp Val
    210                 215                 220

Thr Leu Ala Ile Pro Lys Thr Ser Pro Pro Thr Met Leu Arg Leu
225                 230                 235                 240

Phe Lys Gly Gln Ser Ser Val Val His Val His Leu Lys Arg His Leu
                245                 250                 255

Met Lys Glu Leu Pro Glu Thr Asp Asn Asp Val Ala Gln Trp Cys Lys
            260                 265                 270

Asp Ile Phe Val Ala Lys Asp Asn Leu Leu Asp Lys His Lys Thr Glu
        275                 280                 285

Ser Thr Phe Gly Asp Gln Asp Leu Gln Asp Ile Gly Arg Pro Leu Lys
    290                 295                 300

Ser Leu Leu Val Val Ile Ser Trp Ala Cys Leu Leu Ile Ser Gly Ala
305                 310                 315                 320

Leu Lys Phe Leu Ile Gly Ser Ala Leu Leu Ser Ser Trp Lys Gly Ile
                325                 330                 335

Val Ile Ser Ala Ser Gly Leu Gly Leu Val Thr Val Leu Met Gln Thr
            340                 345                 350

Leu Ile Leu Phe Ser Gln Ser Glu Arg Ser Thr Ser Ala Lys Ile Gly
        355                 360                 365

Ser Ala Asn Gly Glu Glu Arg Arg Thr Lys His Gln
    370                 375                 380

<210> SEQ ID NO 3
<211> LENGTH: 389
<212> TYPE: PRT
<213> ORGANISM: Arabidopsis thaliana

<400> SEQUENCE: 3

Met Val Ile Ala Ala Val Ile Val Pro Leu Gly Leu Leu Phe
1               5                   10                  15

Ile Ser Gly Leu Ala Val Asn Leu Phe Gln Ala Val Cys Tyr Val Leu
            20                  25                  30

Ile Arg Pro Leu Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

```
Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Ser Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Ile Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Thr Ile Pro Lys Thr Ser Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
    290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Thr
                325                 330                 335

Ile Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
        355                 360                 365

Ala Lys Pro Lys Asp Asn His His Pro Glu Ser Ser Ser Gln Thr Glu
    370                 375                 380

Thr Glu Lys Glu Lys
385

<210> SEQ ID NO 4
<211> LENGTH: 390
<212> TYPE: PRT
<213> ORGANISM: Brassica napus

<400> SEQUENCE: 4

Met Ala Met Ala Ala Val Ile Val Pro Leu Gly Ile Leu Phe Phe
1               5                   10                  15

Ile Ser Gly Leu Val Val Asn Leu Leu Gln Ala Val Cys Tyr Val Leu
            20                  25                  30

Val Arg Pro Met Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60
```

```
Gly Val Lys Ile Gln Val Phe Ala Asp Asp Glu Thr Phe Asn Arg Met
 65                  70                  75                  80

Gly Lys Glu His Ala Leu Val Val Cys Asn His Arg Ser Asp Ile Asp
                 85                  90                  95

Trp Leu Val Gly Trp Ile Leu Ala Gln Arg Ser Gly Cys Leu Gly Ser
                100                 105                 110

Ala Leu Ala Val Met Lys Lys Ser Ser Lys Phe Leu Pro Val Ile Gly
                115                 120                 125

Trp Ser Met Trp Phe Ser Glu Tyr Leu Phe Leu Glu Arg Asn Trp Ala
                130                 135                 140

Lys Asp Glu Ser Thr Leu Gln Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
                180                 185                 190

Pro Val Pro Arg Asn Val Leu Ile Pro Arg Thr Lys Gly Phe Val Ser
                195                 200                 205

Ala Val Ser Asn Met Arg Ser Phe Val Pro Ala Ile Tyr Asp Met Thr
                210                 215                 220

Val Ala Ile Pro Lys Thr Ser Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Pro Glu Asp Glu Ile Ala Gln Trp Cys Arg Asp
                260                 265                 270

Gln Phe Val Ala Lys Asp Ala Leu Leu Asp Lys His Ile Ala Ala Asp
                275                 280                 285

Thr Phe Pro Gly Gln Lys Glu Gln Asn Ile Gly Arg Pro Ile Lys Ser
                290                 295                 300

Leu Ala Val Val Ser Trp Ala Cys Leu Leu Thr Leu Gly Ala Met Lys
305                 310                 315                 320

Lys Phe Leu His Trp Ser Asn Leu Phe Ser Ser Trp Lys Gly Ile Ala
                325                 330                 335

Leu Ser Ala Phe Gly Leu Gly Ile Ile Thr Leu Cys Met Gln Ile Leu
                340                 345                 350

Ile Arg Ser Ser Gln Ser Glu Arg Ser Thr Pro Ala Lys Val Ala Pro
                355                 360                 365

Ala Lys Pro Lys Asp Asn His Gln Ser Gly Pro Ser Ser Gln Thr Glu
                370                 375                 380

Val Glu Glu Lys Gln Lys
385                 390

<210> SEQ ID NO 5
<211> LENGTH: 391
<212> TYPE: PRT
<213> ORGANISM: Brassica oleracea

<400> SEQUENCE: 5

Met Ala Met Ala Ala Ala Val Ile Val Pro Leu Gly Ile Leu Phe
 1               5                  10                  15

Phe Ile Ser Gly Leu Val Val Asn Leu Leu Gln Ala Val Cys Tyr Val
                20                  25                  30

Leu Ile Arg Pro Leu Ser Lys Asn Thr Tyr Arg Lys Ile Asn Arg Val
                35                  40                  45
```

Val Ala Glu Thr Leu Trp Leu Glu Leu Val Trp Ile Val Asp Trp Trp
            50                  55                  60

Ala Gly Val Lys Ile Gln Val Phe Ala Asp Asp Glu Thr Phe Asn Arg
 65                  70                  75                  80

Met Gly Lys Glu His Ala Leu Val Val Cys Asn His Arg Ser Asp Ile
                 85                  90                  95

Asp Trp Leu Val Gly Trp Ile Leu Ala Gln Arg Ser Gly Cys Leu Gly
            100                 105                 110

Ser Ala Leu Ala Val Met Lys Lys Ser Ser Lys Phe Leu Pro Val Ile
            115                 120                 125

Gly Trp Ser Met Trp Phe Ser Glu Tyr Leu Phe Leu Glu Arg Asn Trp
            130                 135                 140

Ala Lys Asp Glu Ser Thr Leu Lys Ser Gly Leu Gln Arg Leu Asn Asp
145                 150                 155                 160

Phe Pro Arg Pro Phe Trp Leu Ala Leu Phe Val Glu Gly Thr Arg Phe
                    165                 170                 175

Thr Glu Ala Lys Leu Lys Ala Ala Gln Glu Tyr Ala Ala Thr Ser Gln
                180                 185                 190

Leu Pro Val Pro Arg Asn Val Leu Ile Pro Arg Thr Lys Gly Phe Val
            195                 200                 205

Ser Ala Val Ser Asn Met Arg Ser Phe Val Pro Ala Ile Tyr Asp Met
210                 215                 220

Thr Val Ala Ile Pro Lys Thr Ser Pro Pro Thr Met Leu Arg Leu
225                 230                 235                 240

Phe Lys Gly Gln Pro Ser Val His Val His Ile Lys Cys His Ser
                    245                 250                 255

Met Lys Asp Leu Pro Glu Ser Glu Asp Glu Ile Ala Gln Trp Cys Arg
                260                 265                 270

Asp Gln Phe Val Ala Lys Asp Ala Leu Leu Asp Lys His Ile Ala Ala
            275                 280                 285

Asp Thr Phe Pro Gly Gln Lys Glu Gln Asn Ile Asp Arg Pro Ile Lys
            290                 295                 300

Ser Leu Ala Val Val Val Ser Trp Ala Cys Leu Leu Thr Leu Gly Ala
305                 310                 315                 320

Met Lys Phe Leu His Trp Ser Asn Leu Phe Ser Ser Leu Lys Gly Ile
                    325                 330                 335

Ala Leu Ser Ala Leu Gly Leu Gly Ile Ile Thr Leu Cys Met Gln Ile
                340                 345                 350

Leu Ile Arg Ser Ser Gln Ser Glu Arg Ser Thr Pro Ala Lys Val Ala
            355                 360                 365

Pro Ala Lys Pro Lys Asp Lys His Gln Ser Gly Ser Ser Ser Gln Thr
            370                 375                 380

Glu Val Glu Glu Lys Gln Lys
385                 390

<210> SEQ ID NO 6
<211> LENGTH: 390
<212> TYPE: PRT
<213> ORGANISM: Crambe hispanica

<400> SEQUENCE: 6

Met Ala Met Ala Ala Val Ile Val Pro Leu Gly Ile Leu Phe Phe
1               5                   10                  15

Ile Ser Gly Leu Val Val Asn Leu Leu Gln Ala Ile Cys Tyr Val Leu
            20                  25                  30

Ile Arg Pro Leu Ser Lys Asn Thr Tyr Arg Lys Ile Asn Arg Val Val
            35                  40                  45

Ala Glu Thr Leu Trp Leu Glu Leu Val Trp Ile Val Asp Trp Trp Ala
 50                  55                  60

Gly Val Lys Ile Gln Val Phe Ala Asp Asn Glu Thr Phe Asn Arg Met
 65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Lys Phe Leu Pro Val Ile Gly
            115                 120                 125

Trp Ser Met Trp Phe Ser Glu Tyr Leu Phe Leu Glu Arg Asn Trp Ala
            130                 135                 140

Lys Asp Glu Ser Thr Leu Gln Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
            195                 200                 205

Ala Val Ser Asn Met Arg Ser Phe Val Pro Ala Ile Tyr Asp Met Thr
            210                 215                 220

Val Ala Ile Pro Lys Thr Ser Pro Pro Thr Met Leu Arg Leu Phe
225                 230                 235                 240

Lys Gly Gln Pro Ser Val His Val His Ile Lys Cys His Ser Met
                245                 250                 255

Lys Asp Leu Pro Glu Ser Asp Ala Ile Ala Gln Trp Cys Arg Asp
            260                 265                 270

Gln Phe Val Ala Lys Asp Ala Leu Leu Asp Glu His Ile Ala Ala Asp
            275                 280                 285

Thr Phe Pro Gly Gln Gln Glu Gln Asn Ile Gly Arg Pro Ile Lys Ser
            290                 295                 300

Leu Ala Val Ser Leu Ser Trp Ser Cys Leu Leu Ile Leu Gly Ala Met
305                 310                 315                 320

Lys Phe Leu His Trp Ser Asn Leu Phe Ser Ser Trp Lys Gly Ile Ala
                325                 330                 335

Phe Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
            355                 360                 365

Ala Lys Pro Lys Asp Asn His Asn Asp Ser Gly Ser Ser Ser Gln Thr
            370                 375                 380

Glu Ala Glu Lys Gln Lys
385                 390

<210> SEQ ID NO 7
<211> LENGTH: 377
<212> TYPE: PRT
<213> ORGANISM: Limnanthes douglasii

<400> SEQUENCE: 7

Met Ala Ile Pro Ala Ala Ala Phe Ile Val Pro Ile Ser Leu Leu Phe
 1               5                  10                  15

Phe Met Ser Gly Leu Val Val Asn Phe Ile Gln Ala Val Phe Tyr Val
            20                  25                  30

Leu Val Arg Pro Ile Ser Lys Asp Thr Tyr Arg Arg Ile Asn Thr Leu
        35                  40                  45

Val Ala Glu Leu Leu Trp Leu Glu Leu Val Trp Val Ile Asp Trp Trp
50                  55                  60

Ala Gly Val Lys Val Gln Leu Tyr Thr Asp Thr Glu Ser Phe Arg Leu
65                  70                  75                  80

Met Gly Lys Glu His Ala Leu Leu Ile Cys Asn His Arg Ser Asp Ile
                85                  90                  95

Asp Trp Leu Ile Gly Trp Val Leu Ala Gln Arg Cys Gly Cys Leu Ser
            100                 105                 110

Ser Ser Ile Ala Val Met Lys Lys Ser Lys Phe Leu Pro Val Ile
        115                 120                 125

Gly Trp Ser Met Trp Phe Ser Glu Tyr Leu Phe Leu Glu Arg Asn Trp
130                 135                 140

Ala Lys Asp Glu Asn Thr Leu Lys Ser Gly Leu Gln Arg Leu Asn Asp
145                 150                 155                 160

Phe Pro Lys Pro Phe Trp Leu Ala Leu Phe Val Glu Gly Thr Arg Phe
                165                 170                 175

Thr Lys Ala Lys Leu Leu Ala Ala Gln Glu Tyr Ala Ala Ser Ala Gly
            180                 185                 190

Leu Pro Val Pro Arg Asn Val Leu Ile Pro Arg Thr Lys Gly Phe Val
        195                 200                 205

Ser Ala Val Ser Asn Met Arg Ser Phe Val Pro Ala Ile Tyr Asp Leu
210                 215                 220

Thr Val Ala Ile Pro Lys Thr Glu Gln Pro Thr Met Leu Arg Leu
225                 230                 235                 240

Phe Arg Gly Lys Ser Ser Val Val His Val His Leu Lys Arg His Leu
                245                 250                 255

Met Lys Asp Leu Pro Lys Thr Asp Asp Gly Val Ala Gln Trp Cys Lys
            260                 265                 270

Asp Gln Phe Ile Ser Lys Asp Ala Leu Leu Asp Lys His Val Ala Glu
        275                 280                 285

Asp Thr Phe Ser Gly Leu Glu Val Gln Asp Ile Gly Arg Pro Met Lys
290                 295                 300

Ser Leu Val Val Val Ser Trp Met Cys Leu Leu Cys Leu Gly Leu
305                 310                 315                 320

Val Lys Phe Leu Gln Trp Ser Ala Leu Leu Ser Ser Trp Lys Gly Met
                325                 330                 335

Met Ile Thr Thr Phe Val Leu Gly Ile Val Thr Val Leu Met His Ile
            340                 345                 350

Leu Ile Arg Ser Ser Gln Ser Glu His Ser Thr Pro Ala Lys Thr Arg
        355                 360                 365

Ala Arg Gln Thr Ala Glu Asn Pro Lys
    370                 375

<210> SEQ ID NO 8
<211> LENGTH: 386
<212> TYPE: PRT
<213> ORGANISM: Prunus mume

<400> SEQUENCE: 8

Met Pro Ile Val Ala Ala Val Val Val Pro Leu Gly Leu Leu Phe
1               5                   10                  15

Phe Ile Ser Gly Leu Val Val Asn Leu Ile Gln Ala Ile Cys Phe Ile
            20                  25                  30

Leu Ile Arg Pro Val Ser Lys Asn Leu Tyr Arg Arg Ile Asn Arg Val
        35                  40                  45

Val Ala Glu Leu Leu Trp Leu Glu Leu Val Trp Leu Ile Asp Trp Trp
50                  55                  60

Ala Gly Val Lys Ile Gln Val Tyr Thr Asp His Glu Thr Phe Asn Leu
65                  70                  75                  80

Met Gly Lys Glu His Ala Leu Val Ile Ser Asn His Arg Ser Asp Ile
                85                  90                  95

Asp Trp Leu Val Gly Trp Val Leu Ala Gln Arg Ser Gly Cys Leu Gly
            100                 105                 110

Ser Thr Leu Ala Val Met Lys Lys Ser Lys Phe Leu Pro Val Ile
        115                 120                 125

Gly Trp Ser Met Trp Phe Ser Glu Tyr Leu Phe Leu Glu Arg Ser Trp
    130                 135                 140

Ala Lys Asp Glu Gly Thr Leu Lys Ser Gly Val Gln Arg Leu Lys Asp
145                 150                 155                 160

Phe Pro Gln Pro Phe Trp Leu Ala Leu Phe Val Glu Gly Thr Arg Phe
                165                 170                 175

Thr Gln Ala Lys Leu Leu Ala Ala Gln Glu Tyr Ala Ala Ala Thr Gly
            180                 185                 190

Leu Pro Val Pro Arg Asn Val Leu Ile Pro Arg Thr Lys Gly Phe Val
        195                 200                 205

Thr Ala Val Ser Gln Met Arg Ser Phe Ala Pro Ala Ile Tyr Asp Val
210                 215                 220

Thr Val Ala Ile Pro Lys Ser Ser Pro Ala Pro Thr Met Leu Arg Leu
225                 230                 235                 240

Phe Glu Gly Arg Pro Ser Val Val His Val His Ile Lys Arg His Val
                245                 250                 255

Met Arg Asp Leu Pro Glu Thr Asp Glu Ala Val Ala Gln Trp Cys Lys
            260                 265                 270

Asp Ile Phe Val Ala Lys Asp Ala Leu Leu Asp Lys His Thr Val Glu
        275                 280                 285

Gln Thr Phe Gly Asp Gln Gln Leu Lys Val Thr Gly Arg Pro Leu Lys
290                 295                 300

Ser Leu Leu Val Val Thr Ala Trp Ala Cys Leu Leu Ile Leu Gly Ala
305                 310                 315                 320

Leu Lys Phe Leu Tyr Trp Ser Ser Leu Leu Ser Ser Trp Lys Gly Ile
                325                 330                 335

Ala Phe Ser Ala Leu Gly Leu Gly Val Val Thr Val Leu Met Gln Ile
            340                 345                 350

Leu Ile Arg Phe Ser Gln Ser Glu Arg Ser Thr Pro Ala Ser Val Ala
        355                 360                 365

Pro Ala Asn Asn Asn Lys Gly Glu Ser Ser Gly Lys Pro Glu Lys
370                 375                 380

Gln Gln
385

<210> SEQ ID NO 9
<211> LENGTH: 26
<212> TYPE: DNA
<213> ORGANISM: Artificial Sequence
<220> FEATURE:
<223> OTHER INFORMATION: Primer

```
<400> SEQUENCE: 9
gaggtaccgg aaatgtcagt tgcagc                                              26

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
ccgctcgagt tttactgatg tttggttgc                                           29

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ccggtaccag gatggtgatt gctgcagct                                           29

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
cctcgagtgt gagaaccagt ttttactt                                            28
```